(12) United States Patent
Murakawa et al.

(10) Patent No.: US 8,527,040 B2
(45) Date of Patent: Sep. 3, 2013

(54) HEALTH MANAGING DEVICE

(75) Inventors: Yasuaki Murakawa, Kyoto (JP);
Takehiro Hamaguchi, Kyoto (JP);
Yoshimi Niwa, Nishi Tokyo (JP)

(73) Assignee: Omron Healthcare Co., Ltd.,
Kyoto-Shi (JP)

( * ) Notice: Subject to any disclaimer, the term of this patent is extended or adjusted under 35 U.S.C. 154(b) by 0 days.

(21) Appl. No.: 13/207,942

(22) Filed: Aug. 11, 2011

(65) Prior Publication Data

US 2011/0295144 A1     Dec. 1, 2011

Related U.S. Application Data

(63) Continuation of application No. PCT/JP2010/051804, filed on Feb. 8, 2010.

(30) Foreign Application Priority Data

Mar. 9, 2009    (JP) .................................. 2009-055192

(51) Int. Cl.
*A61B 5/05*    (2006.01)

(52) U.S. Cl.
USPC ....................................................... 600/547

(58) Field of Classification Search
USPC ....................................................... 600/547
See application file for complete search history.

(56) References Cited

U.S. PATENT DOCUMENTS

| | | |
|---|---|---|
| 2002/0052697 A1 | 5/2002 | Serita |
| 2002/0111559 A1 | 8/2002 | Kurata et al. |
| 2005/0222516 A1 | 10/2005 | Kasahara et al. |
| 2006/0025701 A1 | 2/2006 | Kasahara |
| 2008/0243026 A1 | 10/2008 | Tsuji |

FOREIGN PATENT DOCUMENTS

| | | |
|---|---|---|
| DE | 11 2008 000 629 T5 | 12/2009 |
| JP | A-06-78827 | 3/1994 |
| JP | A-07-204164 | 8/1995 |
| JP | A-11-113870 | 4/1999 |
| JP | A-2001-212111 | 8/2001 |
| JP | A-2002-191563 | 7/2002 |
| JP | A-2002-238870 | 8/2002 |
| JP | A-2005-288023 | 10/2005 |
| JP | A-2006-61677 | 3/2006 |
| JP | A-2008-237571 | 10/2008 |
| WO | WO 2008/123044 A1 | 10/2008 |

OTHER PUBLICATIONS

International Search Report dated Apr. 6, 2010 in International Application No. PCT/JP2010/051804 (with translation).

*Primary Examiner* — Brian Szmal
(74) *Attorney, Agent, or Firm* — Oliff & Berridge, PLC

(57) ABSTRACT

In an abdominal fat measuring device that is a health managing device, vertical and horizontal widths of the abdomen of a subject are measured, and an ellipse defined by such widths is defined as an outer shape ellipse. The abdominal fat measuring device stores in advance an image representing the subcutaneous fat of the abdominal back side as an additional image in association with a proportion of the visceral fat mass and the subcutaneous fat mass. In the abdominal fat measuring device, the corresponding image is extracted from the stored additional images from the measured proportion of the visceral fat mass and the subcutaneous fat mass of the subject, added to the outer shape ellipse, and then a figure representing the measured fat free mass, visceral fat mass, and subcutaneous fat mass is drawn and displayed in the outer shape ellipse.

16 Claims, 20 Drawing Sheets

Exceeding portion

Fig. 9

| Impedance (Ω) | Fat thickness (cm) |
|---|---|
| 3 | — |
| 5 | 2 |
| 9 | 4 |

Fig. 13

| Image data | Subject information |
|---|---|
| | Horizontal width: XX11 cm<br>Vertical width: YY11 cm<br>Subcutaneous fat: ZZ1 cm2 |
| | Horizontal width: XX12 cm<br>Vertical width: YY12 cm<br>Subcutaneous fat: ZZ2 cm2 |
| | Horizontal width: XX13 cm<br>Vertical width: YY13 cm<br>Subcutaneous fat: ZZ3 cm2 |

| Image data | Subject information |
|---|---|
|  | Horizontal width: XX21 cm<br>Vertical width: YY21 cm<br>Subcutaneous fat: AA1 cm2 |
|  | Horizontal width: XX22 cm<br>Vertical width: YY22 cm<br>Subcutaneous fat: AA2 cm2 |
|  | Horizontal width: XX23 cm<br>Vertical width: YY23 cm<br>Subcutaneous fat: AA3 cm2 |
| ⋮ | ⋮ |

HEALTH MANAGING DEVICE

TECHNICAL FIELD

The present invention relates to health managing devices, and in particular, to a health managing device for visually outputting measurement results.

BACKGROUND ART

Reducing the accumulation of visceral fat of the visitor is essential in diagnosis, treatment, and improvement of obesity that is the center of lifestyle related disease. Thus, a measuring device for providing the result of the visceral fat measurement with the abdominal cross-sectional image to the visitor and motivating the visitor in motivating the improvement of the lifestyle habit is proposed for the health managing device.

With respect to such measuring device, Japanese Unexamined Patent Publication No. 2002-191563 (hereinafter referred to as patent document 1) discloses a device for creating an image based on the information on the visceral fat area and the subcutaneous fat area, and displaying the same. Specifically, the device disclosed in patent document 1 calculates the visceral fat area and the subcutaneous fat area from the impedance value, the waist peripheral value, and the attribute input value on the abdominal stomach side, and displays the same with the concentric circle.

Patent Document 1: Japanese Unexamined Patent Publication No. 2002-191563

DISCLOSURE OF THE INVENTION

Problems to be Solved by the Invention

However, the device of patent document 1 uses the value obtained by simply measuring the length of the waistline for the waist peripheral value. Since the shape of the abdominal cross-section is different for each person, the shape of the abdominal cross-section cannot be accurately expressed with the length of the waistline. Therefore, the shape of the abdominal cross-section of the visitor cannot be known from only the length of the waistline displayed by the device of patent document 1. Furthermore, the distribution of the visceral fat accumulation cannot be accurately known with the display of the device of patent document 1 since the distribution of the visceral fat accumulation changes by the shape of the abdomen.

In other words, if the visceral fat measuring device disclosed in patent document 1 is used, the measurement result is not provided using the image close to his/her abdominal shape (cross-sectional shape, visceral fat accumulation distribution, subcutaneous fat accumulation shape) to the visitor. The visitor thus cannot accurately know his/her abdominal shape and the accumulation state of the visceral fat, and hence improvement of obesity that is the center of lifestyle related disease is not motivated with respect to the visitor.

In view of the above problems, one object of the present invention is to provide a health managing device for outputting the measurement result in which the abdominal shape of the subject can be easily grasped by representing the abdominal cross-sectional shape and the accumulation mass, and the distribution of the subcutaneous fat and the visceral fat with an image closer to the subject himself/herself.

Means for Solving the Problem

In order to achieve the above aim, in accordance with one aspect of the present invention, a health managing device includes a first measuring device for measuring a vertical width and a horizontal width of a subject, a second measuring device for measuring information related to visceral fat, subcutaneous fat, and fat free mass of the subject using impedance, and a display processing device for executing a process of specifying an abdominal cross-sectional image of the image corresponding to the measurement results of the first measuring device and the second measuring device and displaying the same on a display device.

Effect of the Invention

According to the present invention, the measurement result in the health managing device can be expressed with an image closer to the abdominal shape of the subject.

BRIEF DESCRIPTION OF THE DRAWINGS

FIG. 9 is a view showing a specific example of a conversion table used in a third specific example (display process 1-3) of the display process of step S9 of FIG. 3 according to the first embodiment.

FIG. 13 is a view showing a specific example of information stored in a subcutaneous fat image database of the body fat measuring device main body according to a second embodiment.

BEST MODE FOR CARRYING OUT THE INVENTION

Figure 1:
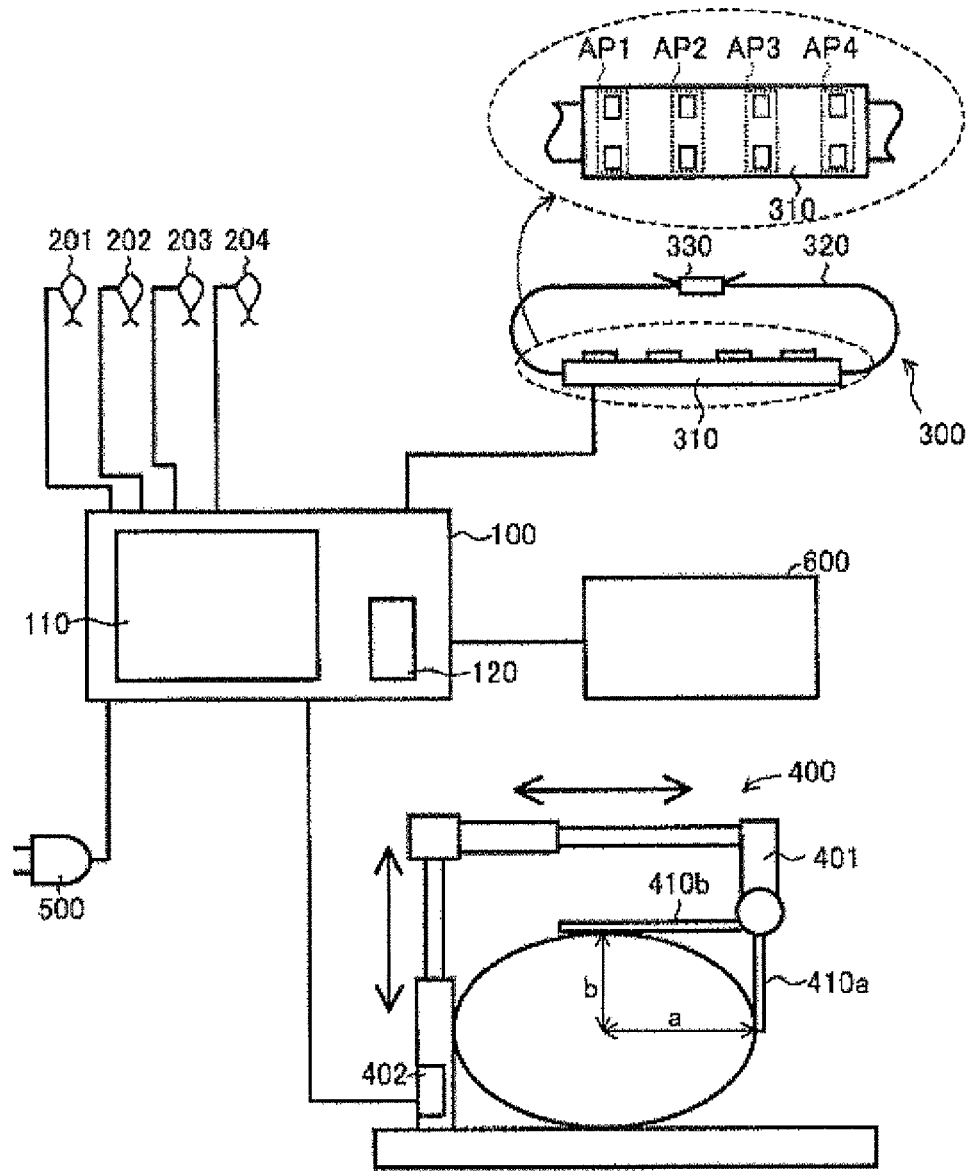
FIG. 1 is a view showing a specific example of a configuration of a body fat measuring device according to the embodiment.

Embodiments of the present invention will be hereinafter described with reference to the drawings. In the following description, the same reference numerals are denoted for the same components and structural elements. The names and functions thereof are the same.

In the following description, a body fat measuring device configured to be able to measure not only the visceral fat mass but also the fat mass of the entire body and the fat mass by specific site of the body (fat mass of upper limb and lower limb, fat mass of trunk, subcutaneous fat mass at abdomen, etc.) will be described by way of example for the health managing device. In other words, the "body fat measuring device" serving as the health managing device includes an "abdomen fat measuring device".

Here, "abdomen" is the portion excluding the breast in the trunk. When referring to "site distant from the abdomen", this includes the upper limb including the upper arm, the forearm, the wrist, and the finger, the breast distant by a predetermined distance (e.g., about 10 cm) or more from the diaphragm, an upper body including the shoulder, the neck, and the head, and the lower limb including the thigh, the lower thigh, the angle, and the toe. The "body axis" is the axis in a direction substantially perpendicular to the transverse plane of the abdomen of the subject. The "abdominal stomach side" includes the visible portion when the subject is observed from the front surface of the abdomen of the subject. For instance, the "abdominal stomach side" includes the visible portion when the subject is observed from the umbilicus side along the axis passing through the umbilicus and the backbone of the subject and being perpendicular to the body axis of the subject of the abdomen of the subject. The "abdominal back side" includes the visible portion when the subject is observed from the back of the abdomen of the subject. For instance, the "abdominal back side" includes the visible portion when the subject is observed from the backbone side along the axis passing through the umbilicus and the backbone of the subject and being perpendicular to the body axis of the subject of the abdomen of the subject. The "vertical width" of the abdomen is the maximum length from the umbilicus side to the abdominal back side of the transverse plane of the abdomen of the subject. The "horizontal width" of the abdomen is the maximum length in an axial direction perpendicular to the axis in a vertical width direction of the transverse plane of the abdomen of the subject.

With reference to FIG. 1, the body fat measuring device (hereinafter referred to as measuring device) according to the present embodiment includes a device main body 100, four clips 201, 202, 203, 204 for attaching electrodes to four limbs to be connected to the device main body 100 by wire or wirelessly, a belt 300 for attaching the electrode to the abdominal back side, a measurement unit 400 for measuring the horizontal width and the vertical width of the abdomen, and an outlet 500 for supplying power to the device main body 100. The horizontal width and the vertical width of the abdomen are expressed as 2a, 2b, respectively, in the example of FIG. 1.

The device main body 100 includes a display section 110 and an operation section 120. The device main body 100 may be connected to an external device 600 by wire or wirelessly to carry out communication. The external device 600 may be a personal computer, a printer, or the like. The device main body 100 has the functions described later, and performs the process of calculating various types of fat masses by detecting the potential difference of each site of the subject, and displaying the same on the display section 110 as measurement results. The LCD (Liquid Crystal Display) can be used for the display section 110. The operation section 120 is a site for the measurer to input commands to the device main body 100, and is configured by keys and the like that can be pushed by the measurer.

The clips 201, 202, 203, 204 includes electrodes H11, H21, F11, F21. The clips 201, 202 respectively include upper limb electrodes H11, H21. The clip 201 is attached to the wrist of the right hand of the subject and the clip 202 is attached to the wrist of the left hand of the subject, so that the upper limb electrodes H11, H21 are respectively attached to the surface of the wrist of the right hand and the surface of the wrist of the left hand. The clips 203, 204 respectively include lower limb electrodes F11, F21. The clip 203 is attached to the ankle of the right foot of the subject and the clip 204 is attached to the ankle of the left foot of the subject, so that the lower limb electrodes F11, F21 are respectively attached to the surface of the ankle of the right foot and the surface of the ankle of the left foot.

The belt 300 includes a pushing member 310 to be pushed against the abdominal back side of the subject, a belt portion 320 fixed to both sides of the pushing member 310, and a buckle 330 for fixing the belt portion 320. The pushing member 310 includes electrode pairs AP1 to AP4. The belt 300 is wrapped around the abdomen of the subject so that the pushing member 310 is positioned slightly on the upper side than the coccyx, so that the electrode pairs AP1 to AP4 are closely attached to the abdominal back side of the subject.

The measurement unit 400 includes a cursor supporting portion 401 and a body build measuring portion 402. The cursor supporting portion 401 includes a member movable in a first direction and a member movable in a second direction orthogonal to the first direction, and supports a horizontal width measurement cursor part 401a and a vertical width measurement cursor part 401b. The horizontal width measurement cursor part 401a is supported parallel to the member movable in the first direction and the vertical width measurement cursor part 401b is supported parallel to the member movable in the second direction by the cursor supporting portion 401. The measurer moves each member of the cursor supporting portion 401 so as to sandwich the transverse plane of the abdomen of the subject with the horizontal width measurement cursor part 401a and the member movable in the first direction and with the vertical width measurement cursor part 401b and the member movable in the second direction with the horizontal width measurement cursor part 401a and the vertical width measurement cursor part 401b brought into contact with the abdomen of the subject. The body built measuring portion 402 is electrically connected to the cursor supporting portion 401 and the device main body 100. The body built measuring portion 402 detects the length of each member of the cursor supporting portion 401 at the timing of accepting the operation of the operation switch (not shown) or detecting elapse of a predetermined time from the start of measurement, and outputs a signal indicating the length of each member to the device main body 100 as body build information related to the shape of the abdominal cross-section of the subject. The vertical and horizontal width of the abdomen of the subject is thereby calculated using the signal from the body build measuring portion 402 in the device main body 100. The vertical and horizontal width of the abdomen of the subject facing up is measured by defining the first direction as a vertical direction and the second direction as a horizontal direction.

In the example shown in FIG. 1, the measurement unit 400 is connected to the device main body 100 and the vertical and horizontal widths of the abdomen of the subject are calculated based on the signal from the measurement unit 400, but the vertical and horizontal widths of the abdomen of the subject measured separately may be input from the operation section 120.

Figure 2:
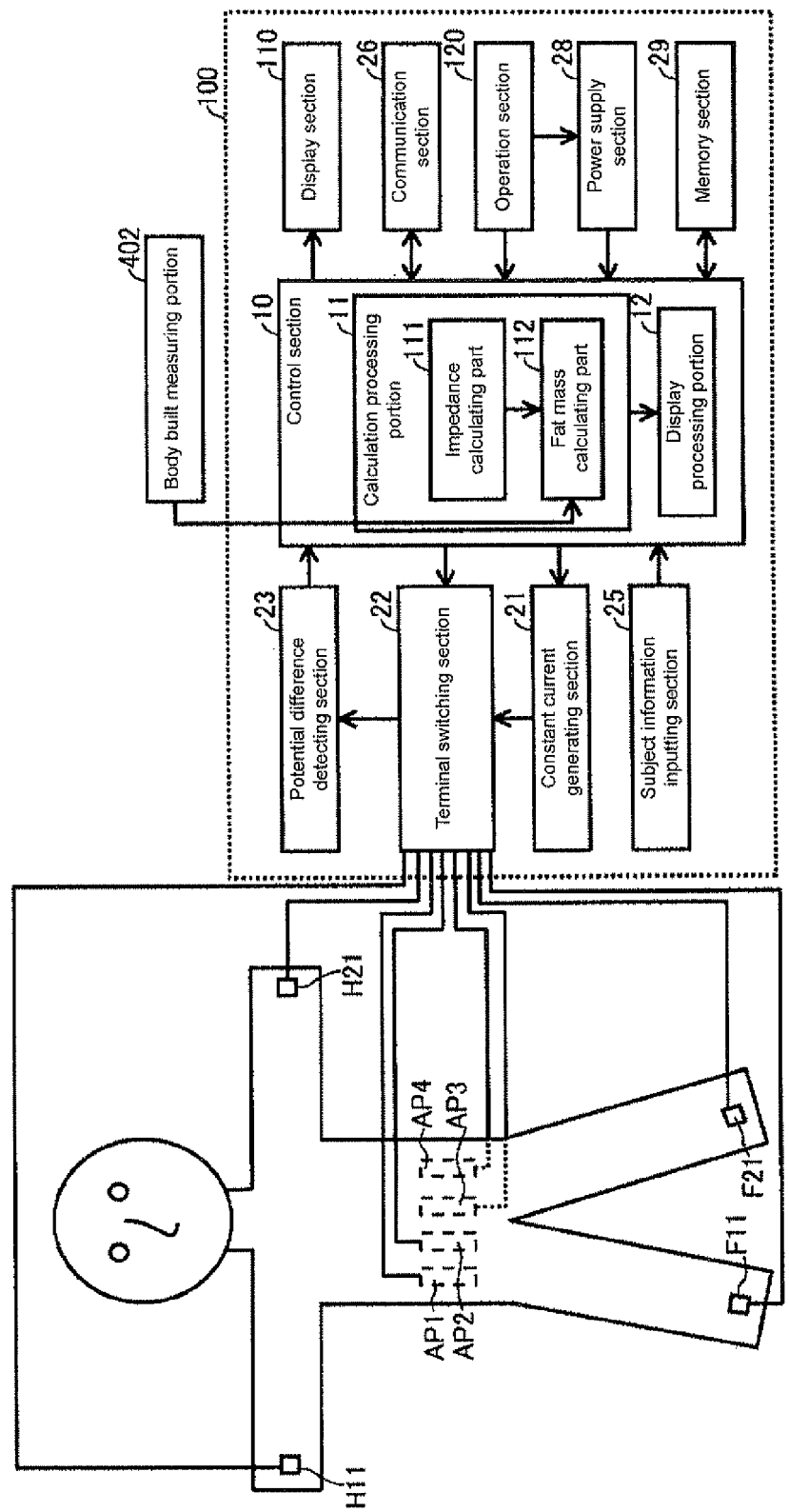
FIG. 2 is a view describing the arrangement of each electrode shown in FIG. 1 to a subject, and the function configuration of a device main body.

With reference to FIG. 2, the device main body 100 includes a control section 10, a constant current generating section 21, a terminal switching section 22, a potential difference detecting section 23, a subject information inputting section 25, a communication section 26, the operation section 120, a power supply section 28, and a memory section 29.

The power supply unit 28 is a site for supplying power to the control section 10, or the like, and includes an internal power supply such as a battery and an external power supply such as a commercial power supply input through the outlet 500.

The memory section 29 is a site for storing various types of data and program related to the device main body 100, and stores the subject information to be described later, the various types of calculated fat masses, the body fat measurement program for executing the body fat measuring process, the display processing program for executing the process of displaying the measurement result.

The control section 10 includes a calculation device such as a CPU (Central Processor Unit), and controls the entire device main body 100. The control section 10 reads out and executes the program stored in the memory section 29 to send a command to various types of function blocks of FIG. 2, perform various calculation processes based on the obtained information, or display the measurement result. The control section 10 includes a calculation processing portion 11 and a display processing portion 12. Such functions may be mainly formed in the CPU by causing the CPU arranged in the control section 10 to execute the program, or at least one part may be formed by other calculation circuits and hardware of the CPU.

The terminal switching section 22 is configured by a plurality relay circuits or the like. The terminal switching section 22 is electrically connected to abdominal electrode pairs AP1 to AP4, upper limb electrodes H11, H21, and the lower limb electrodes F11, F21.

The abdominal electrode pairs AP1, AP2, AP3, and AP4 are arranged in the pushing member 310 of the belt portion 320, and are attached to the surface of the abdominal back side of the subject in a body axis direction by attaching the belt portion 320 to the subject so that the pushing member 310 is brought into contact with the abdominal back side of the subject. The abdominal electrode pairs AP1, AP2, AP3, AP4 are arranged in the body axis direction at the abdominal back side of the subject and are arranged with a space from each other in a direction substantially perpendicular to the body axis. For instance, the abdominal electrode pair AP2 is arranged away by a predetermined distance from the axis passing through the two electrodes of the abdominal electrode pair AP1.

The inter-electrode distance of each abdominal electrode pair AP1, AP2, AP3, AP4 is substantially equal. For instance, the distance between the electrodes of the abdominal electrode pair AP1 and the distance between the electrodes of the abdominal electrode pair AP2 are substantially equal. The two electrodes of the abdominal electrode pairs AP1, AP2, AP3, AP4 are arranged aligned in a direction substantially perpendicular to the electrodes of the corresponding other electrode pair and the body axis.

The terminal switching section 22 electrically connects a specific electrode pair selected from a plurality of electrodes and the constant current generating section 21, and electrically connects a specific electrode pair selected from the plurality of electrodes and the potential difference detecting section 23 based on the command from the control section 10. The electrode pair electrically connected to the constant current generating section 21 by the terminal switching section 22 functions as the constant current application electrode pair, and the electrode pair electrically connected to the potential difference detection section 23 by the terminal switching section 22 functions as a potential difference detection electrode pair. The electric connection by the terminal switching section 22 is variously switched during the measurement operation.

The potential difference detecting section 23 detects the potential difference between the electrodes of the electrode pair, that is, the potential difference detection electrode pair electrically connected to the potential difference detecting section 23 by the terminal switching section 22, and outputs the detected potential difference to the control section 10. Thus, the potential difference between the electrodes of the potential difference detection electrode pair while the constant current is applied to the subject is then detected.

The subject information inputting section 25 is a site for obtaining the subject information used in the calculation process or the like performed in the calculation processing portion 11 of the control section 10. The subject information means the information related to the subject, and includes at least one of the information of age, sex, and body build information. The body build information includes information such as height and weight. The subject information inputting section 25 is a site for inputting the subject information, and outputs the input subject information to the control section 10. In the function block diagram shown in FIG. 2, a case in which the subject information inputting section 25 is arranged in the body fat measuring device is illustrated, but this is not necessarily an essential configuration. Whether or not to arrange the subject information inputting section 25 is appropriately selected based on the type of subject information used in the calculation process or the like performed in the calculation processing portion 11 of the control section 10. The body build information of the subject information may be measured in the measurement unit 400 and input from the body build measuring portion 402, or the body build information may be input by the subject himself/herself in the subject information inputting section 25.

The calculation processing portion 11 includes an impedance calculating part 111 and a fat mass calculating part 112. The impedance calculating part 111 calculates the various impedances based on the current value of the constant current generated by the constant current generating section 21 and the potential difference information detected in the potential difference detecting section 23 and received by the control section 10. The fat mass calculating part 112 calculates various fat masses based on the impedance information obtained in the impedance calculating part 111, the body build information input from the body build measuring portion 402, and the subject information input from the subject information inputting section 25 as necessary. The fat mass calculating part 112 calculates the visceral fat mass of the subject, and the subcutaneous fat mass at the abdomen of the subject. The fat free mass is also calculated based on such values.

The impedance calculating part 111 calculates two types of impedances based on the current value generated in the constant current generating section 21, and the potential difference detected in the potential difference detecting section 23. One of the two types of impedances is the impedance (the impedance is hereinafter referred to as Zt) reflecting the fat free mass at the abdomen of the subject. The other impedance may be the impedance (the impedance is hereinafter referred to as Zs) reflecting the subcutaneous fat mass at the abdomen of the subject.

The fat mass calculating part 112 calculates the visceral fat mass such as the visceral fat area (unit: $cm^2$) of the subject based on the calculated two types of impedances Zt, Zs, and the horizontal width (2a) and the vertical width (2b) of the abdomen of the subject measured in the measurement unit 400. As a specific example, the visceral fat area Sv is calculated by the following equation (1) representing the relationship between the two types of impedances Zt, Zs and the horizontal width (2a) as well as the vertical width (2b) of the abdomen, and the visceral fat area:

$$Sv = \alpha1 \times \pi \times 2a \times 2b - \alpha2 \times Zs \times a - \alpha3 \times 1/Zt - \beta1 \quad (1)$$

(where $\alpha1, \alpha2, \alpha3, \beta1$: coefficient)

The fat mass calculating part 112 calculates the subcutaneous fat mass such as the subcutaneous fat area (unit: $cm^2$) of the subject based on the calculated impedance Zs and the horizontal width (2a) and the vertical width (2b) of the abdomen of the subject measured in the measurement unit 400. As a specific example, the subcutaneous fat area Ss is calculated by the following equation (2) representing the relationship between the impedance Zs, the horizontal width (2a) of the abdomen of the subject, and the subcutaneous fat area:

$$Ss = \alpha4 \times 2a \times Zs + \beta2 \quad (2)$$

(where $\alpha4, \beta2$: coefficient)

The fat mass calculating part 112 calculates the fat free mass such as the fat free area (unit: $cm^2$) of the subject based on the calculated impedance Zt. Specifically, the fat free mass FFM is calculated by the following equation (3) representing the relationship between the impedance Zt and the fat free mass:

$$FFM = \alpha5 \times 1/Zt + \beta3 \quad (3)$$

(where $\alpha5, \beta3$: coefficient)

The coefficient in each equation (1), (2), (3) is defined by the regression formula based on the measurement results by the X-ray CT. The coefficient in each equation (1), (2), (3) may be defined for every age and/or sex.

The constant current generating section 21 flows current between the electrodes of the electrode pair (hereinafter referred to as current electrode pair) electrically connected with the constant current generating section 21 by the terminal switching section 22. The potential difference detecting section 23 detects the potential difference between the electrodes of the electrode pair (hereinafter referred to as voltage electrode pair) electrically connected with the potential difference detecting section 23 by the terminal switching section 22.

Figure 3:
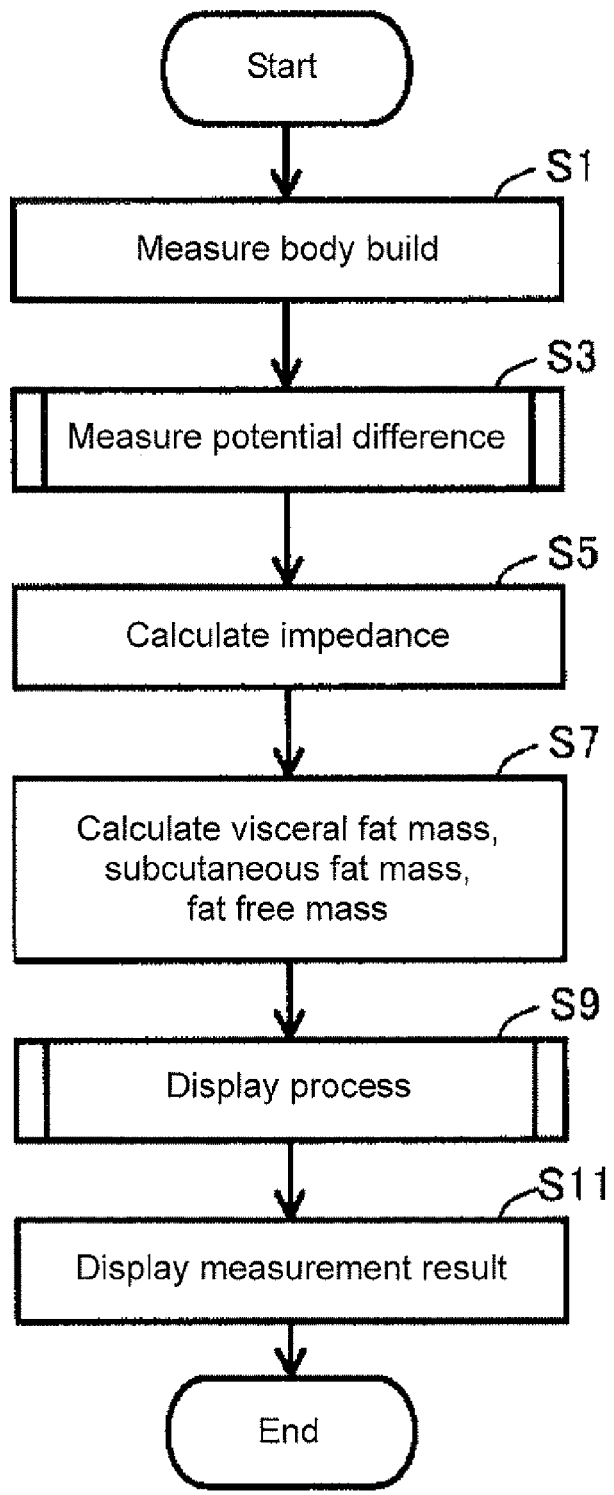
FIG. 3 is a flowchart showing a specific example of the measurement operation in the device main body.

The measurement operation in the device main body 100 will be specifically described using FIG. 3. The operation shown in the flowchart of the FIG. 3 is realized when the control section 10 reads out and executes the program stored in the memory section 29, and controls each section shown in FIG. 2.

With reference to FIG. 3, the control section 10 receives the input of the subject information including the body built information such as the horizontal width and the vertical width (2a, 2b) of the abdomen of the subject measured by the body built measuring portion 402, and the like (step S1). The received subject information is temporarily saved in the memory section 29.

The voltage difference measurement operation is then carried out by the control section 10 (step S3). Specifically, the control section 10 first measures the potential difference to calculate the impedance Zt. In other words, the control section 10 selects a pair of upper limb electrode H11 and lower limb electrode F11 and a pair of upper limb electrode H21 and lower limb electrode F21 as the current electrode pair, and selects the abdominal electrode pair AP1 as the voltage electrode pair. The terminal switching section 22 electrically connects the pair of upper limb electrode H11 and lower limb electrode F11 and the pair of upper limb electrode H21 and lower limb electrode F21 to the constant current generating section 21 based on the control of the control section 10, and electrically connects the abdominal electrode pair AP1 to the potential difference detecting section 23. The terminal switching section 22 disconnects the electrical connection of the non-selected electrode and the constant current generating section 21 and the potential difference detecting section 23 based on the control of the control section 10.

The constant current generating section 21 flows current in a direction from the upper limb to the lower limb based on the control of the control section 10. For instance, the constant current generating section 21 flows current from the upper limb electrode H11 and the upper limb electrode H21 to the lower limb electrode F11 and the lower limb electrode F21. In this case, the terminal switching section 22 preferably has a configuration that short circuits the upper limb electrode H11 and the upper limb electrode H21, and that short circuits the lower limb electrode F11 and the lower limb electrode F21. The constant current generating section 21 and the terminal switching section 22 may have a configuration of flowing current from one of the upper limb electrodes H11, H21 to one of the lower limb electrodes F11, F21. In this state, the potential difference detecting section 23 detects the potential difference between the electrodes of the abdominal electrode pair AP1 based on the control of the control section 10.

The control section 10 selects the abdominal electrode pairs AP2, AP3, AP4 in order as the voltage electrode pair. In other words, the terminal switching section 22 electrically connects the abdominal electrode pairs AP2, AP3, AP4 to the potential difference detecting section 23 in order based on the control of the control section 10. The potential difference detecting section 23 then detects in order the potential difference between the electrodes of each abdominal electrode pair AP2, AP3, AP4 based on the control of the control section 10.

The control section 10 then measures the potential difference to calculate the impedance Zs. In other words, the control section 10 selects the abdominal electrode pair AP1 as the current electrode pair, and selects the abdominal electrode pair AP2 as the voltage electrode pair. The terminal switching section 22 electrically connects the abdominal electrode pair AP1 to the constant current generating section 21 and electrically connects the abdominal electrode pair AP2 to the potential difference detecting section 23 based on the control of the control section 10. The terminal switching section 22 electrically connects each abdominal electrode pair to the potential difference detecting section 23 selectively, and disconnects the electrical connection of the non-selected abdominal electrode pair, the upper limb electrode and the lower limb electrode, and the constant current generating section 21 and the potential difference detecting section 23 based on the control of the control section 10. The constant current generating section 21 flows current between the electrodes of the abdominal electrode pair AP1 based on the control of the control section 10. In this state, the potential difference detecting section 23 detects the potential difference between the electrodes of the abdominal electrode pair AP2 based on the control of the control section 10.

The control section 10 then selects the abdominal electrode pair AP2 as the current electrode pair, and selects the abdominal electrode pair AP1 as the voltage electrode pair. In other words, the terminal switching section 22 electrically connects the abdominal electrode pair AP2 to the constant current generating section 21 and electrically connects the abdominal electrode pair AP1 to the potential difference detecting section 23 based on the control of the control section 10. The constant current generating section 21 flows current between the electrodes of the abdominal electrode pair AP2 based on the control of the control section 10. In this state, the potential difference detecting section 23 detects the potential difference between the electrodes of the abdominal electrode pair AP1 based on the control of the control section 10.

The control section 10 then selects the abdominal electrode pair AP3 as the current electrode pair, and selects the abdominal electrode pair AP4 as the voltage electrode pair. In other words, the terminal switching section 22 electrically connects the abdominal electrode pair AP3 to the constant current generating section 21 and electrically connects the abdominal electrode pair AP4 to the potential difference detecting section 23 based on the control of the control section 10. The constant current generating section 21 flows current between the electrodes of the abdominal electrode pair AP3 based on the control of the control section 10. In this state, the potential difference detecting section 23 detects the potential difference between the electrodes of the abdominal electrode pair AP4 based on the control of the control section 10.

The control section 10 then selects the abdominal electrode pair AP4 as the current electrode pair, and selects the abdominal electrode pair AP3 as the voltage electrode pair. In other words, the terminal switching section 22 electrically connects the abdominal electrode pair AP4 to the constant current generating section 21 and electrically connects the abdominal electrode pair AP3 to the potential difference detecting section 23 based on the control of the control section 10. The constant current generating section 21 flows current between the electrodes of the abdominal electrode pair AP4 based on the control of the control section 10. In this state, the potential difference detecting section 23 detects the potential difference between the electrodes of the abdominal electrode pair AP3 based on the control of the control section 10.

The impedance calculating part 111 calculates the impedance Zt based on the measurement result of the potential difference for calculating the impedance Zt and calculates the impedance Zs based on the measurement result of the potential difference for calculating the impedance Zs (step S5).

In other words, after the potential difference measurement for calculating the impedance Zt, the impedance calculating part 111 calculates the impedances Zt1 to Zt4 based on the current value flowed by the constant current generating section 21 and each potential difference detected by the potential difference detecting section 23 when a detection of the potential difference with respect to all the combinations of the electrode pairs is completed, that is, when a detection of the potential difference between the electrodes of each abdominal electrode pair AP1, AP2, AP3, AP4 is completed. The values of the impedances Zt1 to Zt4 calculated by the impedance calculating part 111 are temporarily saved in the memory section 29.

After the potential difference measurement for calculating the impedance Zs, the impedance calculating part 111 calculates the impedances Zs1 to Zs4 based on the current value flowed by the constant current generating section 21 and each potential difference detected by the potential difference detecting section 23 when the application of the current and the detection of the potential difference with respect to all the combinations of the electrode pairs is completed. The values of the impedances Zs1 to Zs4 calculated by the impedance calculating part 111 are temporarily saved in the memory section 29.

The fat mass calculating part 112 then calculates the visceral fat mass Sv, the subcutaneous fat mass Ss, and the fat free mass FFM as the fat mass based on the body build information received by the control section 10 in step S1 and the impedance calculated in step S5 (step S7).

The visceral fat area Sv is calculated by equation (1) using the body build information and the impedances Zt1 to Zt4 and the impedances Zs1 to Zs4. Here, the average value of the four impedances Zt1 to Zt4 is substituted to the impedance Zt in equation (1), and the average value of the four impedances Zs1 to Zs4 is substituted to the impedance Zs in equation (1).

The subcutaneous fat area Ss is calculated by equation (2) using the body build information and the impedances Zs1 to Zs4. The average value of the four impedances Zs1 to Zs4 is substituted to the impedance Zs in equation (2).

The fat free mass FFM is calculated by equation (3) using the impedances Zt1 to Zt4. The average value of the four impedances Zt1 to Zt4 is substituted to the impedance Zt in equation (3).

The display processing portion 12 performs a process of displaying the fat mass calculated in step S7 on the display section 110 as measurement result (step S9), so that the measurement result is displayed on the display section 110 (step S11). In this example, the measurement result is displayed on the display section 110 in step S11, but the data for display generated by the process of step S9 may be output to the printer, the PC, or the like serving as the external device 600.

The body fat measuring process in the device main body 100 is then terminated.

The typical value of the impedances Zt1 to Zt4 is about 5Ω respectively. The typical value of the impedances Zs1 to Zs4 is about 15Ω respectively.

A specific display process in step S9 will be described below.

First Embodiment

Figure 4:
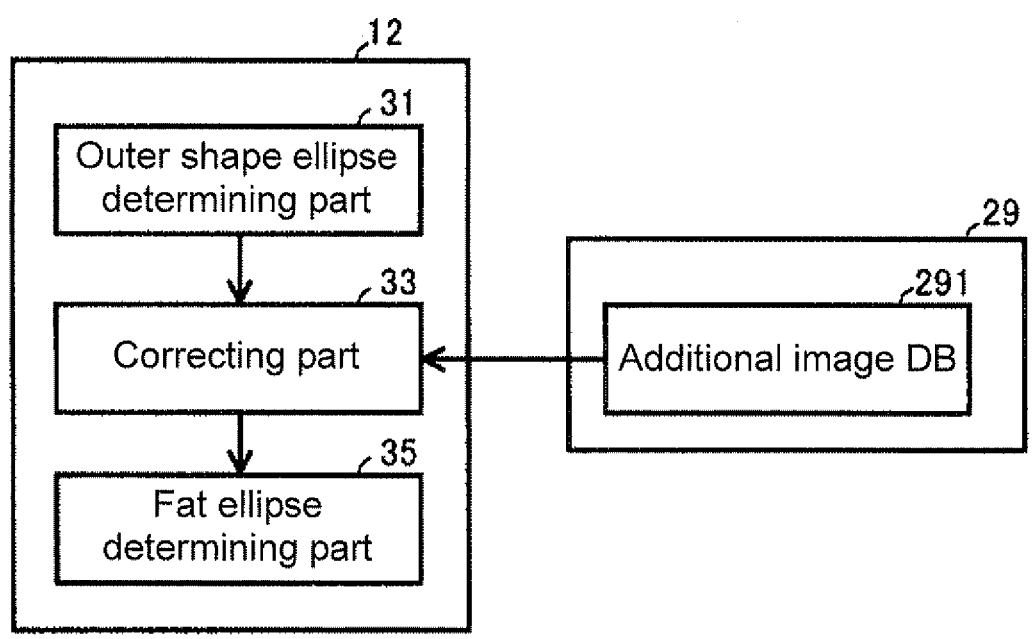
FIG. 4 is a block diagram showing a specific example of a configuration of a display processing portion of a body fat measuring device main body according to a first embodiment.

With reference to FIG. 4, in the first embodiment, the display processing portion 12 includes an outer shape ellipse determining part 31, a correcting part 33, and a fat ellipse determining part 35. These functions may be mainly formed in the CPU by causing the CPU arranged in the control section 10 to execute the display processing program stored in the memory section 29, or at least one part may be formed by other calculation circuits or hardware of the CPU. Furthermore, in the first embodiment, the memory section 29 includes an additional image database (DB) 291 that is a region for storing additional image.

The "outer shape ellipse" refers to an ellipse for display in which the ratio between the horizontal width ($2a$) and the vertical width ($2b$) of the abdomen of the subject is the ratio (ellipticity) of the major axis and the minor axis. The outer shape ellipse can be referred to as a shape in which the subcutaneous fat on the abdominal back side from the side to the back in the abdominal cross-section of the subject is not accurately expressed. The "additional image" is an image representing the subcutaneous fat on the abdominal back side in the abdominal cross-section of the subject. In the abdominal cross-section, the subcutaneous fat mass at the back portion is assumed to be greater as the subcutaneous fat mass increases with respect to the visceral fat mass. Therefore, the additional image has greater area as the subcutaneous fat mass increases with respect to the visceral fat mass. In the additional image DB 291, the additional image is stored in advance in association with the proportion of the visceral fat mass and the subcutaneous fat mass in the first example.

The outer shape ellipse determining part 31 determines the outer shape ellipse used to display the measurement result of the subject based on the horizontal width (2*a*) and the vertical width (2*b*) of the abdomen that is the body build information of the subject input from the body build measuring portion 402. The correcting part 33 performs a process of correcting the outer shape ellipse determined by the outer shape ellipse determining part 31 to become a shape closer to the abdominal cross-section of the subject. In this case, the additional image stored in the additional image DB 291 is used. The fat ellipse determining part 35 determines the elliptical shape based on the shape of the outer shape ellipse to visually display the fat mass calculated by the fat mass calculating part 112 as the measurement result of the subject.

Figure 5:
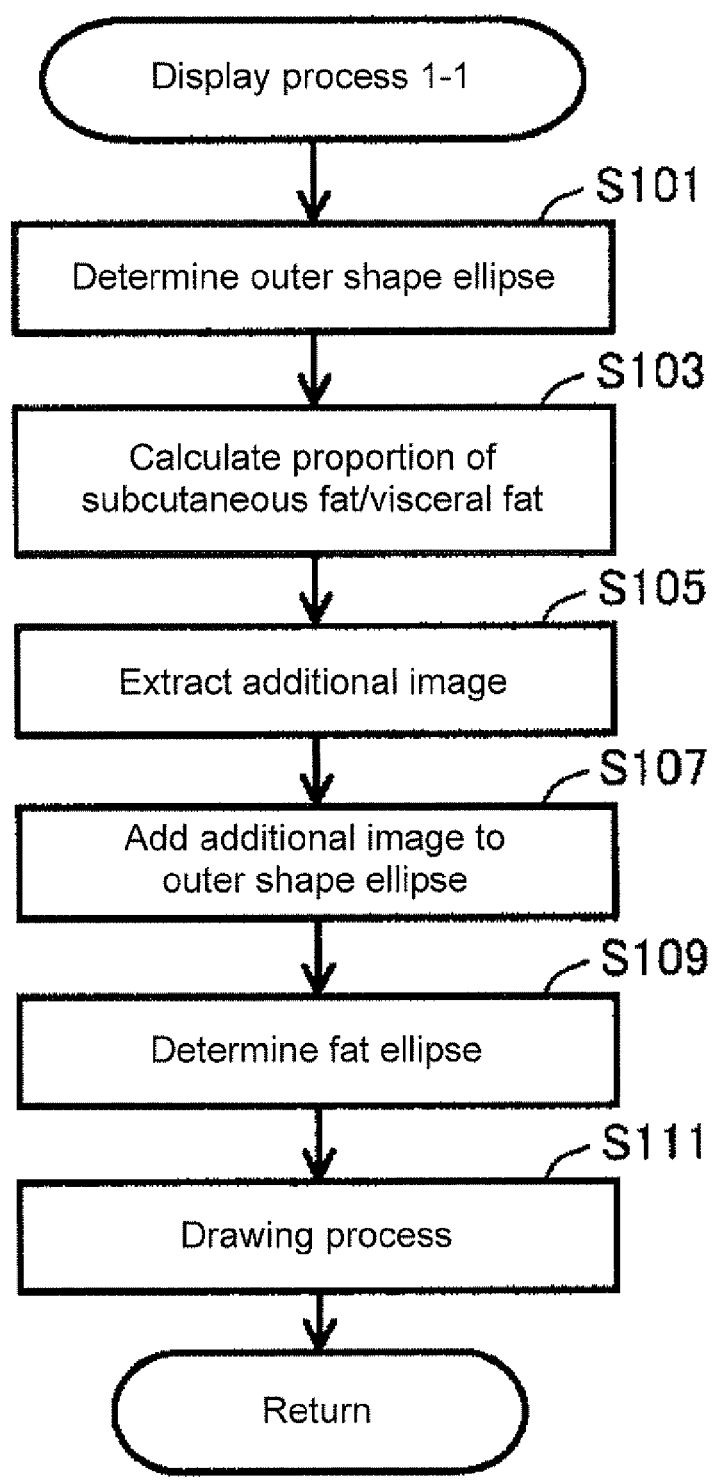
FIG. 5 is a flowchart showing a first specific example (display process 1-1) of the display process of step S9 of FIG. 3 according to the first embodiment.
Figure 6:
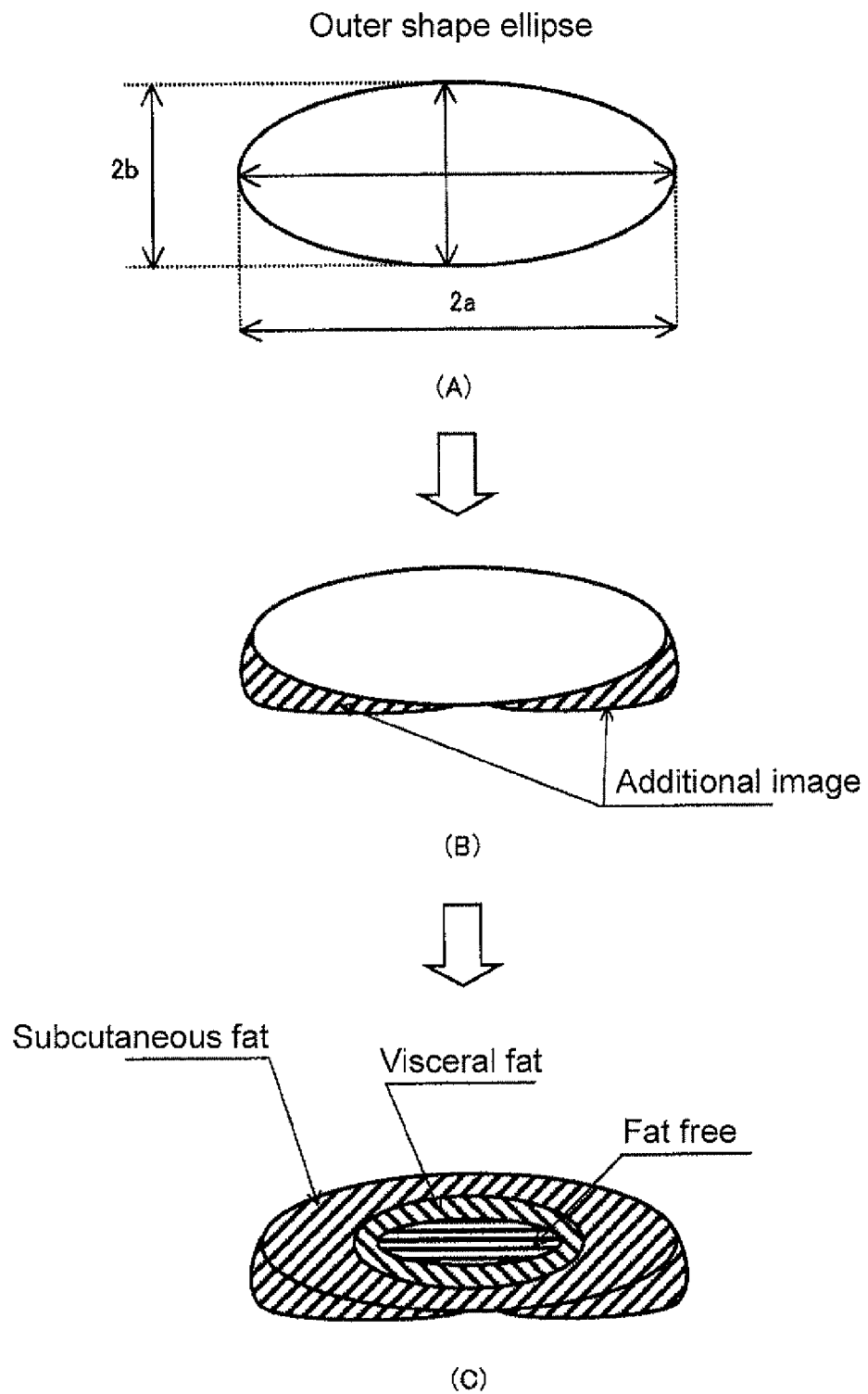
FIGS. 6A and 6B are views describing the flow of the display process 1-1.

A first specific example (display process 1-1) of the display process of step S9 and the flow of the display process 1-1 according to the first embodiment will be described using FIG. 5 and FIGS. 6A and 6B. With reference to FIG. 5, in step S101, the outer shape ellipse determining part 31 determines the outer shape ellipse used to display the measurement result of the subject shown in FIG. 6A based on the horizontal width (2*a*) and the vertical width (2*b*) of the abdomen of the subject measured by the body build measuring portion 402 in step S1. As shown in FIG. 6A, in step S101, the outer shape ellipse determining part 31 determines an ellipse in which the ratio of the major axis and the minor axis is equal to the ratio of the horizontal width (2*a*) and the vertical width (2*b*) of the abdomen of the subject as the outer shape ellipse close to the outer shape of the subject, the transverse diameter being the major axis and the longitudinal diameter being the minor axis. In step S101, one of the diameters (e.g., major axis) of the outer shape ellipse is fixed to a predetermined value in advance, so that the outer shape ellipse determining part 31 may determine the outer shape ellipse by determining the other diameter (e.g., minor axis) based on the ratio of the horizontal width (2*a*) and the vertical width (2*b*) of the abdomen of the subject. In this case, a plurality of types of additional images corresponding to the length of the fixed diameter is preferably stored in the additional image DB 291.

In step S103, the correcting part 33 calculates the proportion of the subcutaneous fat mass and the visceral fat mass calculated by the fat mass calculating part 112 in step S7, extracts the additional image stored in association with the proportion from the additional image DB 291 in step S105, and adds the same to the outer shape ellipse determined in step S101 as shown in FIG. 6B in step S107 to correct the outer shape ellipse determined in step S101. The outer shape close to the abdominal cross-sectional of the subject is thereby formed.

In step S109, the fat ellipse determining part 35 calculates the ratio of each fat mass with respect to the sum of the subcutaneous fat mass, the visceral fat mass, and the fat free mass (hereinafter simply referred to as "sum") calculated by the fat mass calculating part 112 in step S7, and determines the ellipse having the center same as the outer shape ellipse that represents the ratio with respect to the sum of each fat mass with the outer shape ellipse as the sum as shown in FIG. 6C. As shown in FIG. 6C, when representing the fat free mass, the visceral fat mass, and the subcutaneous fat mass in order from the inside, the fat ellipse determining part 35 determines the ellipse in which the value obtained by dividing the major axis and the minor axis of the outer shape ellipse with the ratio with respect to the sum of the fat free mass is set as the major axis and the minor axis as the ellipse (ellipse 1) representing the fat free mass in step S109. The fat ellipse determining part 35 then determines the ellipse in which the value obtained by dividing the major axis and the minor axis of the outer shape ellipse with the ratio with respect to the sum of the fat free mass and the visceral fat mass is set as the major axis and the minor axis as the ellipse (ellipse 2) representing the fat free mass and the visceral fat mass. The ellipse 1 and the ellipse 2 are overlapped on the outer shape ellipse with the center position being the same to represent the ratio of the fat free mass, the visceral fat mass, and the subcutaneous fat mass in order from the inside.

In step S111, the display processing portion 12 performs a process of drawing to define the figure for measurement result display shown in FIG. 6C obtained through the above processes as display data, and terminates a series of processes. In step S111, the drawing may be carried out to display the measurement value of the subcutaneous fat mass or the like, and the value (proportion etc.) obtained by calculating the measurement value in addition to the figure shown in FIG. 6C.

Figure 7:
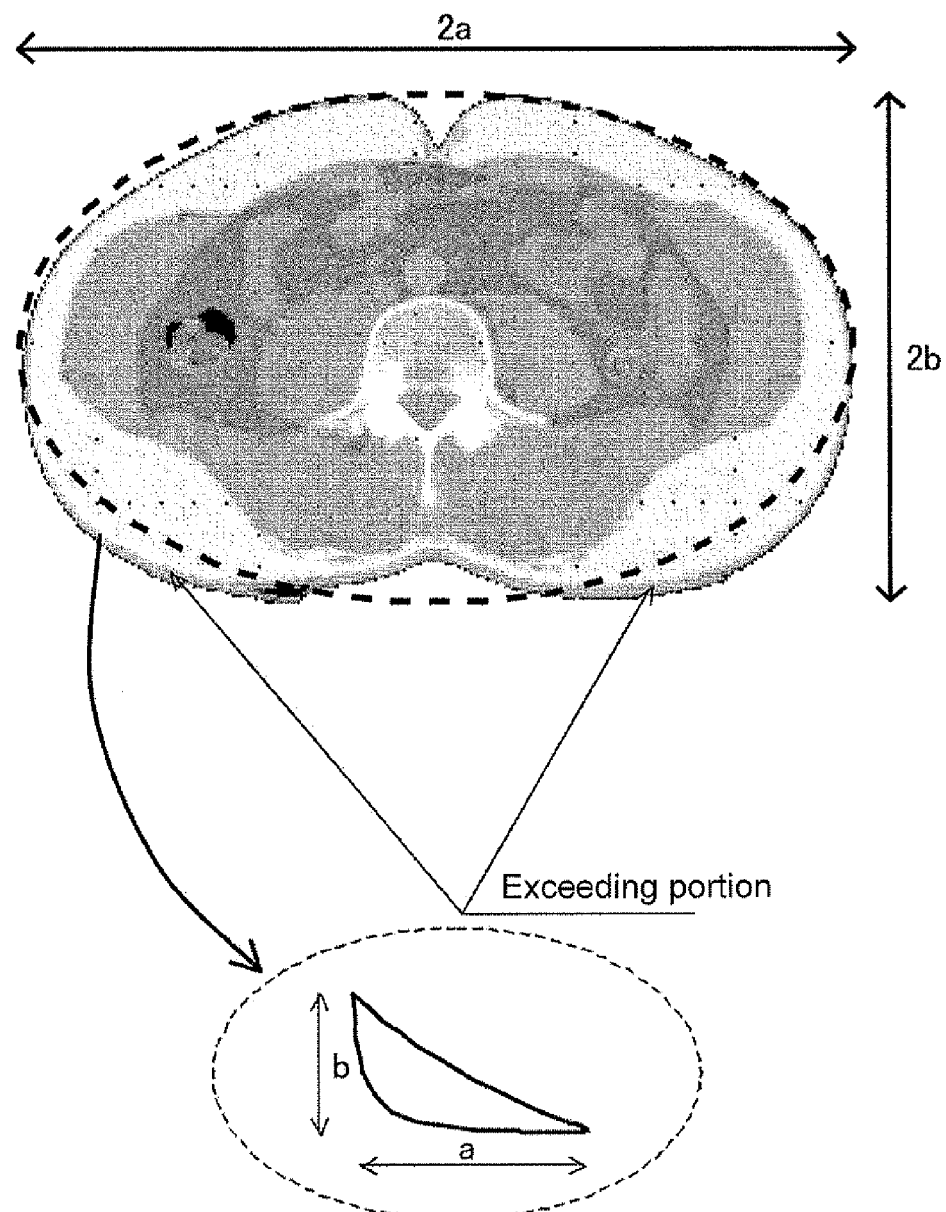
FIG. 7 is a view describing the principle of a second specific example (display process 1-2) of the display process of step S9 of FIG. 3 according to the first embodiment.

The principle of a second specific example (display process 1-2) of the display process of step S9 according to the first embodiment will be described using FIG. 7. FIG. 7 is a view in which a CT (Computed Tomography) image of the abdominal cross-section and the outer shape ellipse are displayed in an overlapped manner. As shown in FIG. 7, the actual abdominal cross-section includes a subcutaneous fat portion at the abdominal back side, and such portion exceeds the ellipse. That is, the elliptical area obtained with the vertical and horizontal widths of the abdomen of the subject does not reflect the subcutaneous fat portion on the abdominal back side, and the difference between the actual cross-sectional area of the actual abdomen corresponding to the total area in a case where the subcutaneous fat mass, the visceral fat mass and the fat free mass are all calculated in area and the elliptical area represents the subcutaneous fat area on the abdominal back side. The subcutaneous fat portion on the abdominal back side lacking in the outer shape ellipse includes the area of such difference, and can be represented with the shape shown in FIG. 7 in which the shape is defined by the horizontal width (2*a*) and the vertical width (2*b*) of the abdomen of the subject, that is, defined with the area of the difference and the horizontal width (2*a*) and the vertical width (2*b*) of the abdomen of the subject as parameters. Therefore, the outer shape ellipse can be corrected to a shape close to the abdominal cross-section of the subject by adding the image specified with such parameters to the outer shape ellipse as an additional image. As a second example, the additional image is stored in advance in the additional image DB 291 in association with the difference area, and the horizontal width and the vertical width of the abdomen of the subject, i.e., the parameters.

Figure 8:
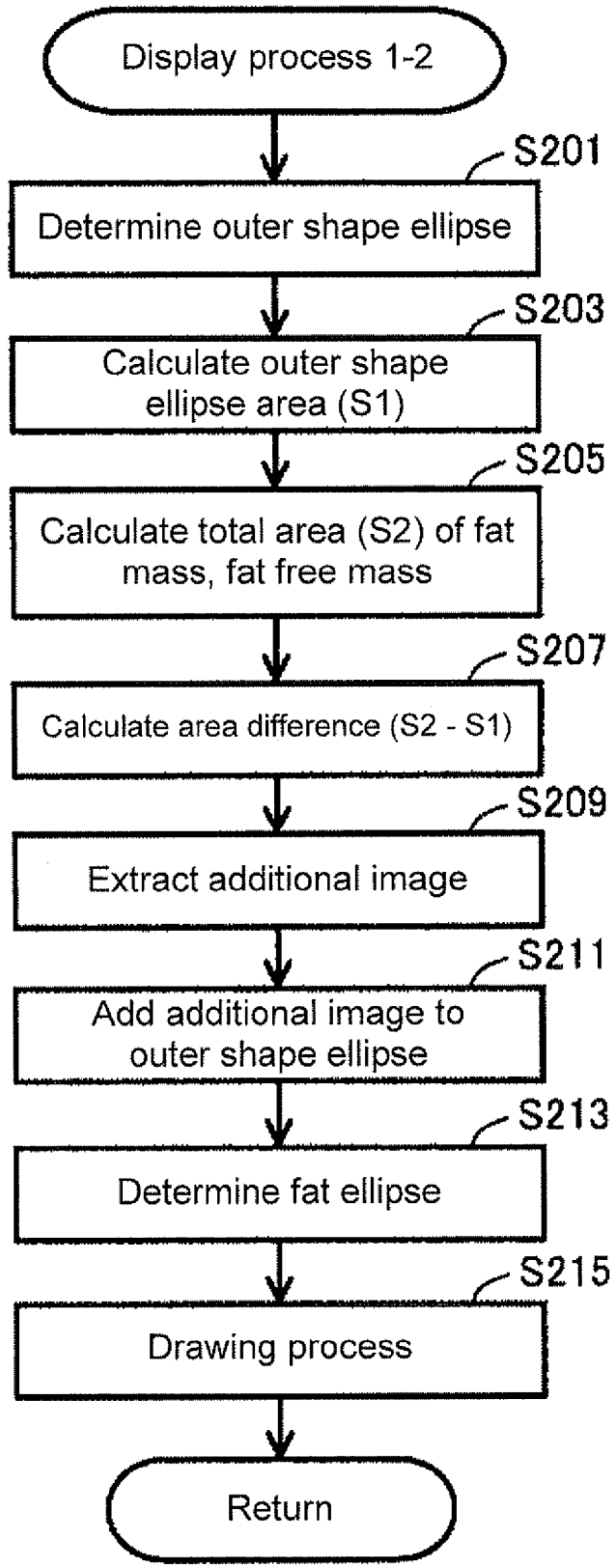
FIG. 8 is a flowchart showing the display process 102.

The display process 1-2 will be described using FIG. 8. With reference to FIG. 8, in step S201, the outer shape ellipse determining part 31 determines the outer shape ellipse based on the horizontal width (2*a*) and the vertical width (2*b*) of the abdomen of the subject measured in the body build measuring portion 402 in step S1. The process here is the same as step S101 of the display process 1-1.

In step S203, the correcting part 33 calculates the area (S1) of the ellipse defining the horizontal width (2a) and the vertical width (2b) of the subject as the major axis and the minor axis, respectively, corresponding to the outer shape ellipse determined in step S201 to correct the outer shape ellipse determined in step S101. In step S205, the sum (S2) of each area of the subcutaneous fat mass, the visceral fat mass, and the fat free mass calculated by the fat mass calculating part 112 in step S7 is calculated. In step S207, the correcting part 33 calculates the difference between the area S1 and the area S2.

In step S209, the correcting part 33 extracts from the additional image DB 291 the additional image stored in association with the difference in area (S2−S1) calculated in step S207 and the horizontal width (2a) and the vertical width (2b) of the abdomen of the subject measured by the body build measuring portion 402 in step S1, and adds the same to the outer shape ellipse determined in step S201 in step S211. The outer shape close to the abdominal cross-section of the subject is thereby formed.

Thereafter, processes same as steps S109 and S111 of the display process 1-1 are performed in steps S213 and S215, and the series of processes are terminated.

Figure 9:
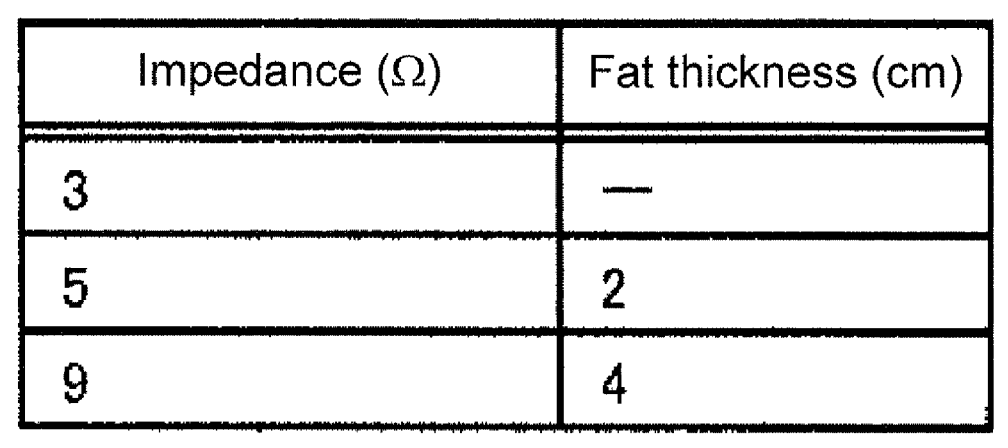

As a third specific example of the display process of step S9 according to the first embodiment, the memory section 29 includes a region for storing a conversion table shown in FIG. 9 in place of the additional image DB 291. The conversion table shown in FIG. 9 is a table in which the correspondence of the impedance value and the fat thickness is defined, and is used to convert the impedance value calculated by the impedance calculating part 111 to the thickness of the subcutaneous fat at the relevant position.

Figure 10:
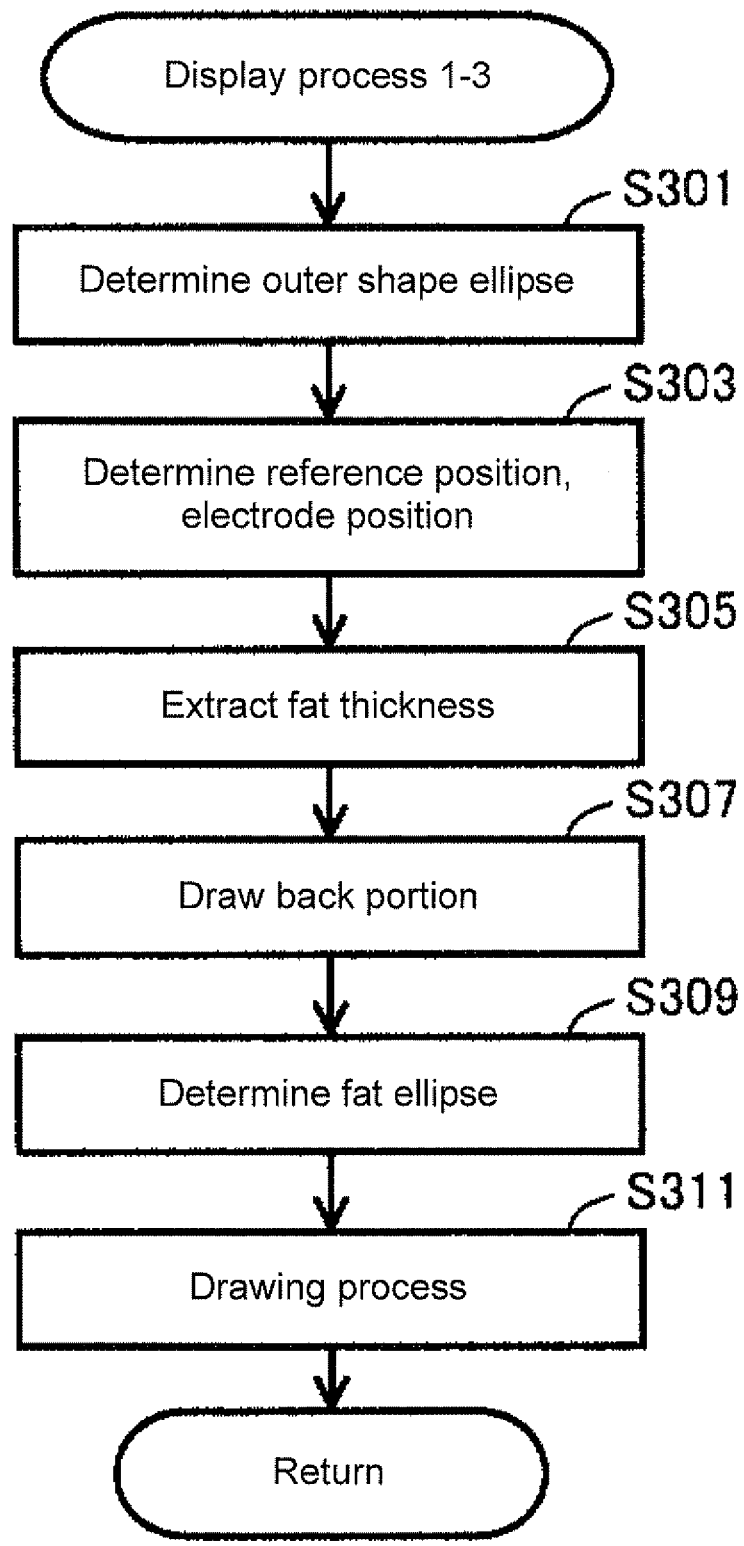
FIG. 10 is a flowchart showing the display process 1-3.
Figure 11:
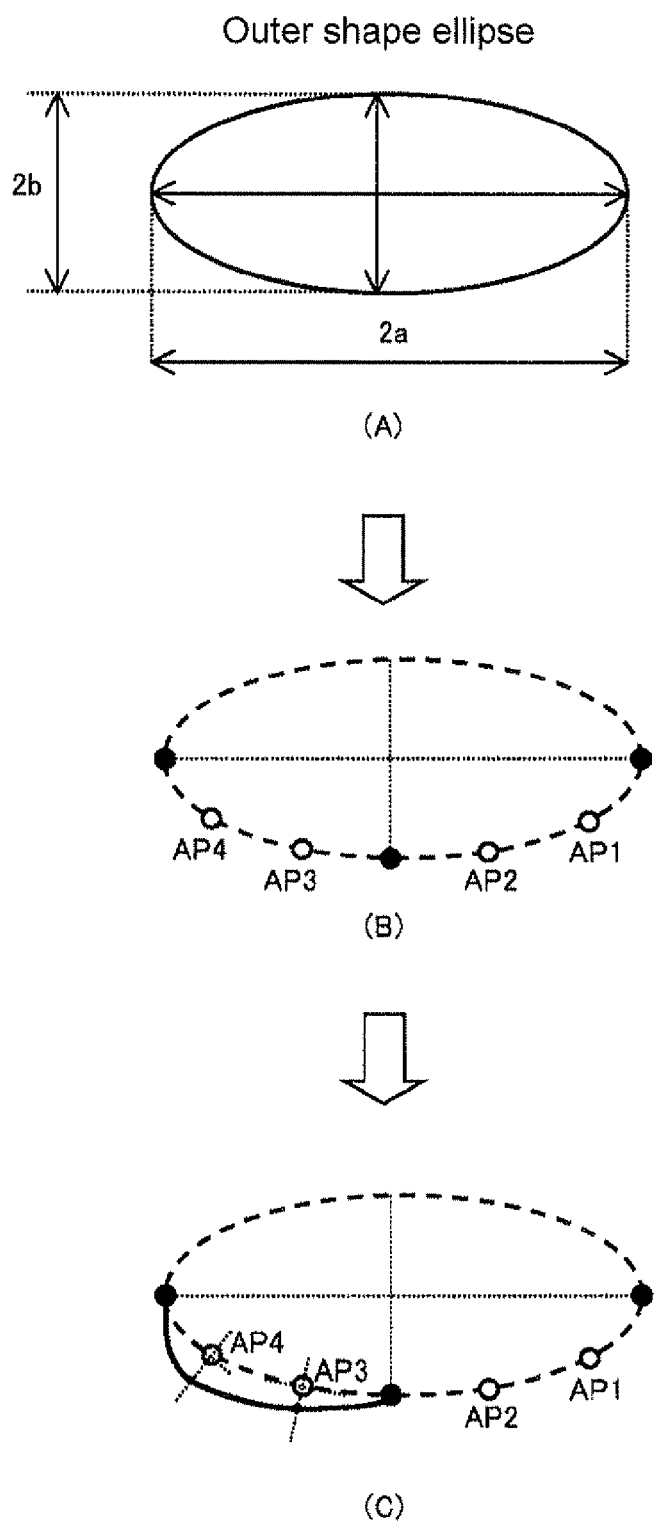
FIGS. 11A and 11B are views describing the flow of the display process 1-3.

The third specific example (display process 1-3) of the display process of step S9 and the flow of the display process 1-3 according to the first embodiment will be described using FIG. 10 and FIGS. 11A and 11B. With reference to FIG. 10, in step S301, the outer shape ellipse determining part 31 determines the outer shape ellipse shown in FIG. 11A based on the horizontal width (2a) and the vertical width (2b) of the abdomen of the subject measured by the body build measuring portion 402 in step S1. The process here is the same as step S101 of the display process 1-1.

In step S303, the correcting part 33 determines the reference position and the electrode position on the outer shape ellipse. The reference position may be three points, the two intersecting points with the axis passing through the focus and one intersecting point with an axis orthogonal to the above axis indicated with a black circuit in FIG. 11B of the four vertices of the outer shape ellipse. As described above, the electrode pairs AP1 to AP4 are pushed against the abdominal back side by the belt 300. For the electrode position on the outer shape ellipse, the position corresponding to each electrode pair indicated with a white circle in FIG. 11B is determined as the electrode position assuming that each electrode pair equally divides the arc length of the ellipse between the vertices.

In step S305, the correcting part 33 extracts the fat thickness at each electrode position determined in step S303 from the conversion table shown in FIG. 9 based on the impedances Zs1 to Zs4 corresponding to the electrode pairs AP1, AP2, AP3, AP4 calculated in the impedance calculating part 111 in step S5, and draws the shape of the abdominal back side in step S307. As a specific example of the drawing of step S307, the fat thickness extracted from the conversion table in step S305 is plotted as the fat position in each electrode position of the outer shape ellipse thus drawing a three dimensional spline curve connecting the reference positions and the fat positions at each electrode position, as shown in FIG. 11C. The three dimensional spline curve is not the sole case, and the reference positions and the fat position at each electrode position may be sequentially connected with a line segment.

Subsequently, the processes same as steps S109 and S111 of the display process 1-1 are performed in steps S309 and S311, and a series of processes are terminated.

When the display processes 1-1 to 1-3 described above are executed by the display processing portion 12 of the device main body 100 according to the first embodiment, the proportion of the subcutaneous fat, the visceral fat, and the like can be displayed in the image of a shape reflecting the measurement result, that is, a shape close to the abdominal cross-section of the subject. In this case, the measurer can more accurately grasp the measurement result of the subject by simultaneously displaying the measurement value and the proportion of the subcutaneous fat etc. In particular, the shape of the subcutaneous fat portion on the abdominal back side, i.e., the position where the belt 300 is attached can be expressed in the processes described above. According to such display, the measurer can accurately grasp the state of the subcutaneous fat, the visceral fat, and the like of the subject compared to when the measurement results are simply displayed within a circle or an ellipse, so that the subject is effectively motivated to improve obesity, which is the center of lifestyle related disease.

In the above description, the electrode pairs AP1 to AP4 are closely attached to the abdominal back side of the subject by attaching the belt 300 such that the pushing member 310 is pushed against the abdominal back side of the subject as also shown in FIG. 2. Therefore, the portion corresponding to particularly the abdominal back side of the outer shape ellipse is corrected by the correcting part 33 for the subcutaneous fat assuming that the subcutaneous fat of the back surface of the subject is measured. However, the belt 300 may be attached so that the electrode pairs AP1 to AP4 are closely attached to other portions of the abdomen such as the abdominal stomach side. In this case, the correcting part 33 corrects the portion corresponding to the abdominal stomach side as the position corresponding to the electrode pairs AP1 to AP4 of the outer shape ellipse. The operation section 120 of the device main body 100 preferably includes keys or the like for inputting the position where the electrode pairs AP1 to AP4 are attached. The correcting part 33 corrects the positions corresponding to the electrode pairs AP1 to AP4 of the outer shape ellipse based on the input of the keys through the method described above. The shape closer to the abdominal cross-section of the subject can be displayed in this manner as well, similar to the display processes 1-1 to 1-3, so that the measurer can more accurately grasp the measurement result of the subject.

Second Embodiment

Figure 12:
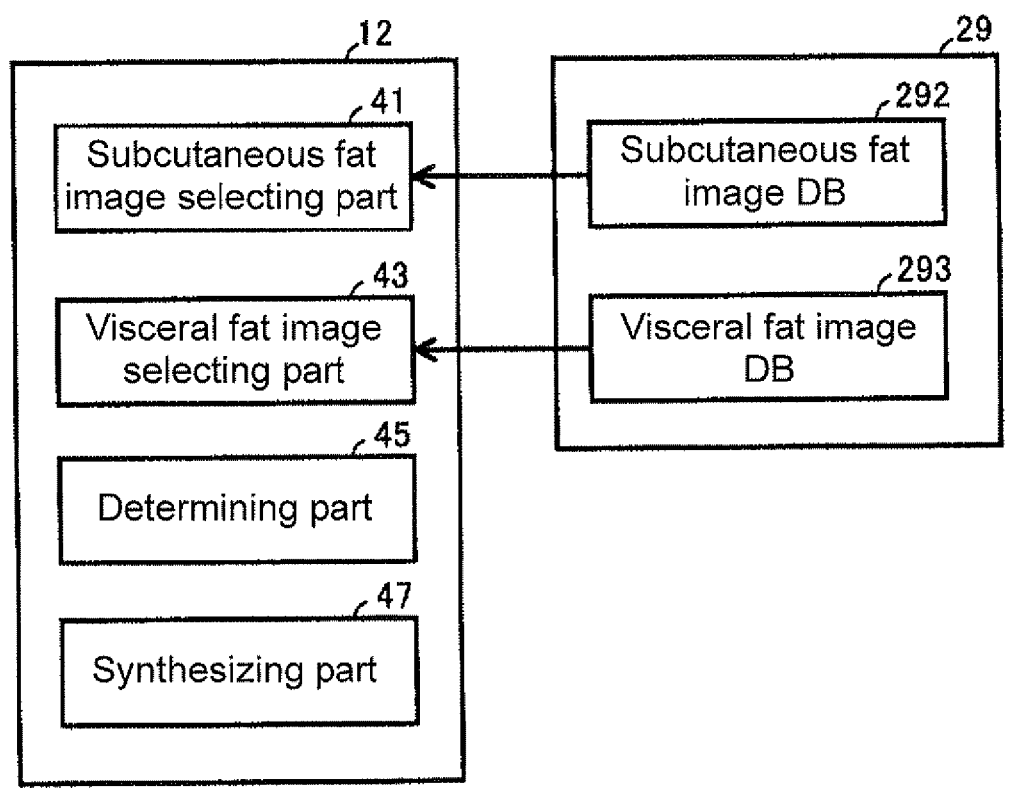
FIG. 12 is a block diagram showing a specific example of a configuration of a display processing portion of a body fat measuring device main body according to a second embodiment.

With reference to FIG. 12, in the second embodiment, the display processing portion 12 includes a subcutaneous fat image selecting part 41, a visceral fat image selecting part 43, a determining part 45, and a synthesizing part 47. These functions may be mainly formed in the CPU by causing the CPU arranged in the control section 10 to execute the display processing program stored in the memory section 29, or at least one part may be formed by other calculation circuits or hardware of the CPU. Furthermore, in the second embodiment, the memory section 29 includes a subcutaneous fat image DB 292 that is a region for storing the subcutaneous fat image, to be described later, and a visceral fat image DB 293 that is a region for storing the visceral fat image, to be described later.

The "subcutaneous fat image" refers to the image in which the image portion representing the visceral fat and the fat free of the CT image of the abdominal cross-section is erased by image processing, and refers to an image having the same shape as the abdominal cross-section and in which the subcutaneous fat is represented as existing over the entire abdominal cross-section. The "visceral fat image" refers to the image showing the portion of the visceral fat and the fat free of the CT image of the abdominal cross-section. The CT image of the abdominal cross-section may be virtually obtained by overlapping the visceral fat image on the subcutaneous fat image.

Figure 14:
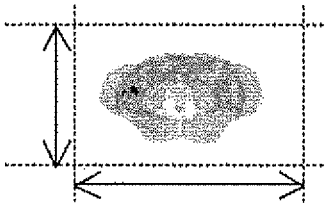
FIG. 14 is a view showing a specific example of information stored in a visceral fat image database of the body fat measuring device main body according to a second embodiment.
Figure 14:
Figure 14:

In the second embodiment, the subcutaneous fat image and the visceral fat image are respectively stored in the subcutaneous fat image DB 292 and the visceral fat image DB 293 in advance. As shown in FIG. 13 and FIG. 14, the image data and the subject information are stored in association to each other in the subcutaneous fat image DB 292 and the visceral fat image DB 293. Specifically, with reference to FIG. 13, the subcutaneous fat image DB 292 stores a plurality of image data in association with the vertical and horizontal widths of the abdomen of the subject of the CT image that becomes the original of the subcutaneous fat image and the subcutaneous fat mass (subcutaneous fat area) measured for the relevant subject as the subject information for every data of the subcutaneous fat image. With reference to FIG. 14, the visceral fat image DB 293 stores a plurality of image data in association with the vertical and horizontal widths of the abdomen of the subject of the CT image that becomes the original of the visceral fat image and the visceral fat mass (visceral fat area) measured for the relevant subject as the subject information for every data of the visceral fat image. Such image data are stored in each DB in advance. Furthermore, the subject information associated with the image data are measured when taking the CT image, and are associated when storing the image data in the DB.

On the basis of the horizontal width (2a) and the vertical width (2b) that are the body build information of the subject input from the body build measuring portion 402 and the subcutaneous fat mass of the subject calculated by the fat mass calculating part 112, the subcutaneous fat image selecting part 41 selects the subcutaneous fat image associated with the subject information closest to such values from the subcutaneous fat images stored in the subcutaneous fat image DB 292 as an image used to display the measurement results of the subject. On the basis of the horizontal width (2a) and the vertical width (2b) that are the body build information of the subject input from the body build measuring portion 402 and the visceral fat mass of the subject calculated by the fat mass calculating part 112, the visceral fat image selecting part 43 selects the visceral fat image associated with the subject information closest to such values from the visceral fat images stored in the visceral fat image DB 293 as an image used to display the measurement results of the subject.

The determining part 45 compares the selected subcutaneous fat image and the visceral fat image, and determines the appropriateness of combining the same. The determining part 45 outputs a control signal instructing the selection of the appropriate image to the subcutaneous fat image selecting pad 41 and/or the visceral fat image selecting part 43 depending on the determination result. The synthesizing part 47 synthesizes the selected subcutaneous fat image and the visceral fat image according to the determination of the determining part 45.

Figure 15:
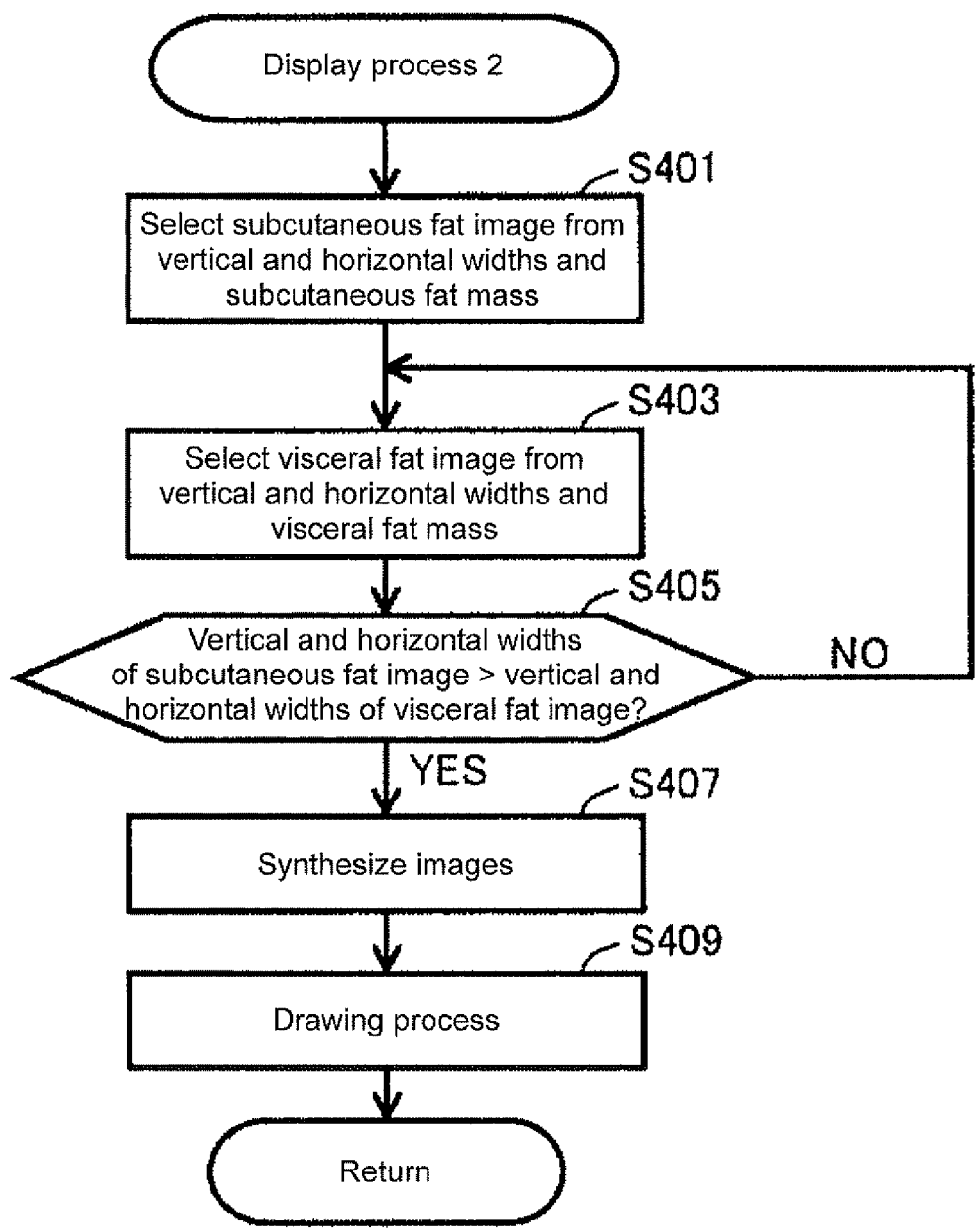
FIG. 15 is a flowchart showing a specific example (display process 2) of the display process of step S9 of FIG. 3 according to the second embodiment.
Figure 16:
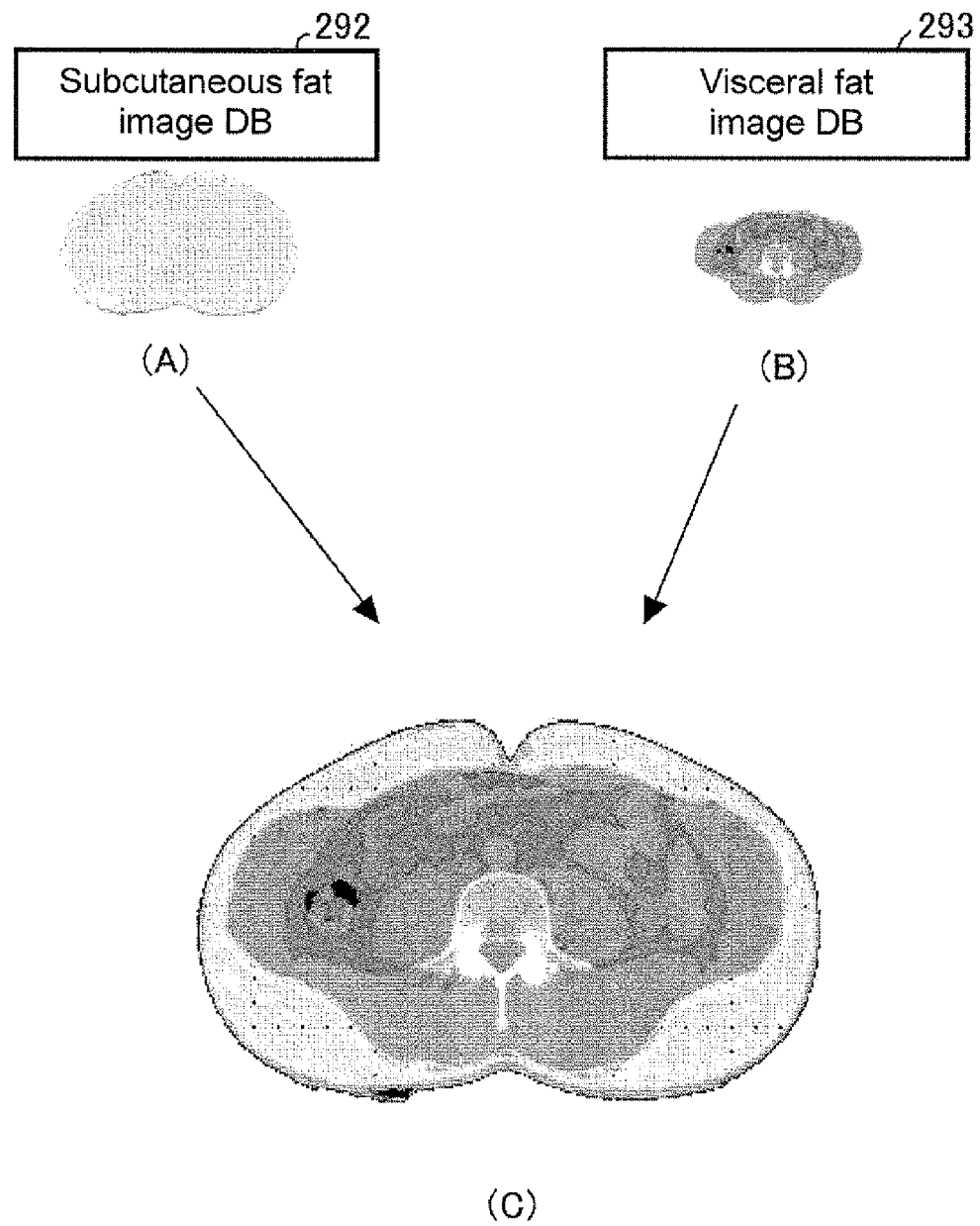
FIGS. 16A to 16C are views describing the flow of the display process 2.

A specific example (display process 2) of the display process of step S9 according to the second embodiment and the flow of the display process 2 will be described using FIG. 15 and FIGS. 16A to 16C. With reference to FIG. 15, in step S401, the subcutaneous fat image selecting part 41, based on the horizontal width and the vertical width of the abdomen of the subject measured by the body build measuring portion 402 in step S1 and the subcutaneous fat mass calculated by the fat mass calculating part 112 in step S7, selects the subcutaneous fat image associated with the subject information closest to such values from the subcutaneous fat image DB 292 (FIG. 16A). In step S403, the visceral fat image selecting part 43, based on the horizontal width and the vertical width of the abdomen of the subject measured by the body build measuring portion 402 in step S1 and the visceral fat mass calculated by the fat mass calculating part 112 in step S7, selects the visceral fat image associated with the subject information closest to such values from the visceral fat image DB 293 (FIG. 16B).

In step S405, the determining part 45 determines the appropriateness of combining the subcutaneous fat image selected in step S401 and the visceral fat image selected in step S403. Specifically, determination is made by comparing the vertical and horizontal widths of the abdomen of the subject of the CT image that are the subject information associated with such images, respectively, and checking whether or not the vertical and horizontal widths associated with the visceral fat image are smaller than the vertical and horizontal widths associated with the subcutaneous fat image. If the vertical and horizontal widths associated with the visceral fat image are greater than the vertical and horizontal widths associated with the subcutaneous fat image, the visceral fat image may exceed the abdominal cross-section if the images are overlapped. Therefore, in step S405, the vertical and horizontal widths of the abdomen of the subject of the information associated with the image data are used to check the adequacy of the size of the subcutaneous fat image and the visceral fat image.

If determined that the combination of the images is inappropriate in the determining part 45 in step S405 (YES in step S405), the process is returned to step S403, and the visceral fat image selecting part 43 selects the visceral fat image associated with the subject information next close to the horizontal width (2a) and the vertical width (2b) that are the body build information of the subject input from the body build measuring portion 402, and the visceral fat mass of the subject calculated in the fat mass calculating part 112. The selection of step S403 is repeated until the determining part 45 determines that the overlapping is appropriate in step S405, and the visceral fat image associated with the subject information close to the measured vertical and horizontal widths and the visceral fat mass of the subject is selected in order.

If determined that the combination of such images is appropriate in the determining part 45 (YES in step S405), the synthesizing part 47 performs the image synthesizing process to overlap the visceral fat image on the subcutaneous fat image in step S407 (FIG. 16(C)). In step S409, the display processing portion 12 performs a process of drawing to define the figure for measurement result display shown in FIG. 16(C) obtained in the above processes as the display data, whereby a series of processes is terminated.

The processing order of step S401 and step S403 may be reversed. In this case, if determined that the overlapping of the selected subcutaneous fat image and the visceral fat image is inappropriate in the determining part 45 in step S405, the operation of selecting the subcutaneous fat image may be repeated in the subcutaneous fat image selecting part 41 until an appropriate image is selected.

In the above example, the visceral fat image is overlapped on the subcutaneous fat image in step S407 to generate the display data, but the image synthesizing process is not always necessary, and the display data of displaying the subcutaneous fat image and the visceral fat image determined in the processes up to now without overlapping may be generated.

The display process 2 described above is executed in the display processing portion 12 of the device main body 100 according to the second embodiment, so that the CT image closer to the subject can be provided based on the measurement value obtained through the impedance method even if the CT photographing function is not mounted on the device main body 100 or the CT photographing device is not connected. With such display, the measurer can visually grasp the state of the subcutaneous fat, the visceral fat, or the like of the subject compared to when the measurement result is displayed only with numerical values and graphs, and hence the motivation of improving the obesity that is the center of the lifestyle related disease is effectively carried out with respect to the subject.

In the second embodiment, the subcutaneous fat image and the visceral fat image are separately stored in the DB, and are respectively configured by selecting and overlapping the image close to the abdominal cross-section of the subject based on the body build information and the measurement result of the subject. Thus, the image closer to the abdominal cross-section of the subject can be provided with fewer number of data compared to when simply storing the image data of the abdominal cross-section itself. Thus, the storage capacity of the memory section 29 can be suppressed, and the size and cost can be suppressed.

In the above example, the vertical and horizontal widths of the abdomen of the subject and the measured subcutaneous fat mass (area) of the subject are associated as the subject information to the subcutaneous fat image data in the subcutaneous fat image DB 292, but the subject information associated to the image data is not limited to such information. For instance, the visceral fat mass, the fat free mass, the ratio of the subcutaneous fat mass and the visceral fat mass, the ratio of the subcutaneous fat mass and the fat free mass, the ratio of the visceral fat mass and the fat fee mass, the plurality of information thereof, and the like may be associated. In this case, the subcutaneous fat image selecting part 41 selects the corresponding subcutaneous fat image using the associated value or calculating the associated proportion of the fat mass calculated in step S7 in step S401. The subcutaneous fat image data may be associated with information such as sex, age, height, or weight of the subject. In this case, the subcutaneous fat image selecting part 41 can select the corresponding subcutaneous fat image by further using the above information of the subject received from the subject information inputting section 25 in step S401. This is the same for the visceral fat image.

Therefore, when the image data close to such information of the subject is selected as the subject information associated with the stored image data increases, the selected image becomes closer to the shape of the abdominal cross-section of the subject.

The visceral fat image data may be grouped for every constant range of the vertical and horizontal widths of the abdomen of the subject and stored in advance in the visceral fat image DB 293. In step S403, the visceral fat image selecting part 43 then can select the visceral fat image from the group suited to the vertical and horizontal widths of the abdomen of the subject associated with the subcutaneous fat image selected in step S401, and the determination of step S405 can be omitted.

Furthermore, in the above example, either one of the images is re-selected when determined that the combination is inappropriate in step S405, but the synthesizing part 47 may carry out synthesizing after performing image processing to reduce (or enlarge) one image so as to be suited to the size of the other image based on the vertical and horizontal widths of the subject associated with both images. The number of image data stored in the DB then can be further suppressed.

Third Embodiment

Figure 17:
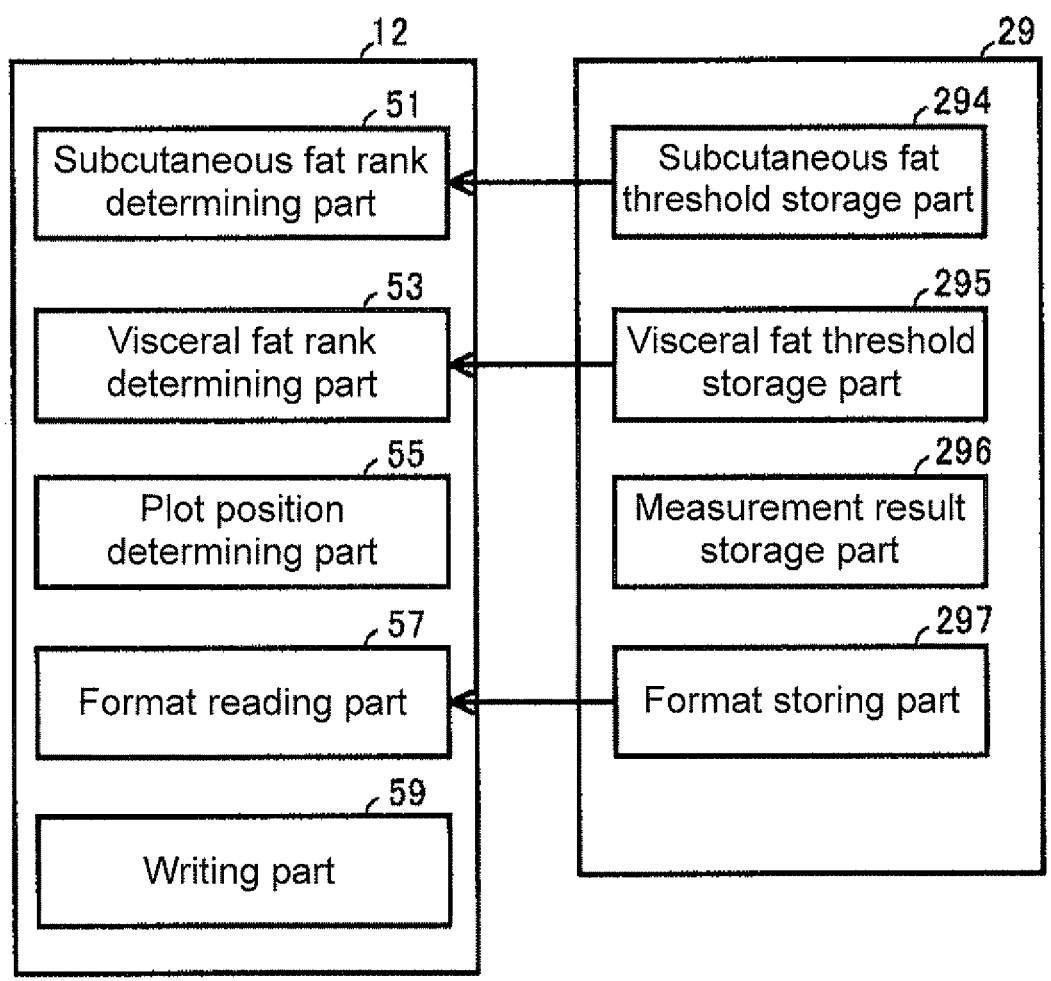
FIG. 17 is a block diagram showing a specific example of a configuration of a display processing portion of the body fat measuring device main body according to a third embodiment.

With reference to FIG. 17, in the third embodiment, the display processing portion 12 includes a subcutaneous fat rank determining part 51, a visceral fat rank determining part 53, a plot position determining part 55, a format reading part 57, and a writing part 59. Such functions may be mainly formed in the CPU by causing the CPU arranged in the control section 10 to execute the program for display processing stored in the memory section 29, or at least one part may be formed by other calculation circuits and hardware of the CPU. Furthermore, in the second embodiment, the memory section 29 includes a subcutaneous fat threshold storage part 294 that is a region for storing the subcutaneous fat threshold value to be described later, a visceral fat threshold storage part 295 that is a region for storing the visceral fat threshold value to be described later, a measurement result storage part 296 for storing measurement results such as visceral fat mass calculated as a result of the measurement, and a format storing part 297 for storing a display format to be described later. The format data showing the format of FIG. 18 is stored in advance in the format storing part 297.

Figure 18:
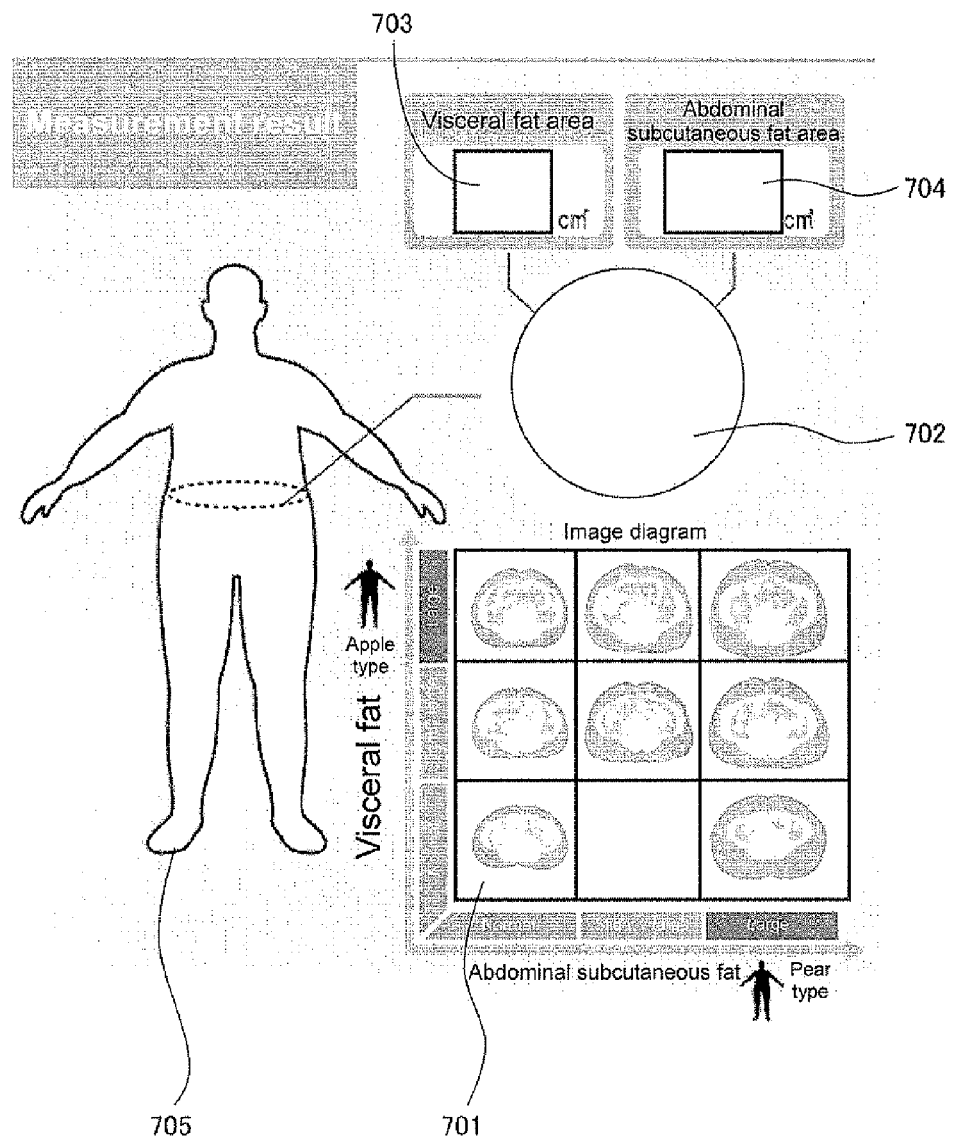
FIG. 18 is a view showing a specific example of a format used in the display in the third embodiment.

With reference to FIG. 18, the format used in the display in the third embodiment includes a region 701 that uses the subcutaneous fat mass and the visceral fat mass of the measurement results as indices to display the measurement result as the position on the matrix defined in the rank of each index, a region 702 for displaying the CT image of the abdominal cross-section stored in advance in correspondence with the measurement result of the subject as an image diagram, a region 703 for displaying the visceral fat area and a region 704 for displaying the subcutaneous fat area of the abdomen as measurement values, and a region 705 for displaying a human silhouette showing the abdomen that is the approximate measurement position of the subject. The CT image of a plurality of representative abdominal cross-sectional corresponding to each position of the matrix of the region 701 is also stored as the format data. The format reading part 57 reads out the format data from the format storing part 297 in display process.

The subcutaneous fat threshold storage part 294 and the visceral fat threshold storage part 295 stores the threshold values for ranking necessary for the matrix display in the region 701 as the subcutaneous fat threshold value and the visceral fat threshold value, respectively. The threshold values here may be a specific fat mass (area etc.) or may be a proportion (e.g., area ratio) with respect to the entire abdomen.

The subcutaneous fat rank determining part 51 and the visceral fat rank determining part 53 compare the measured subcutaneous fat mass and the visceral fat mass with the threshold values stored in the subcutaneous fat threshold storage part 294 and the visceral fat threshold storage part 295, respectively, to determine the rank of each index. The plot position determining part 55 determines the plot position representing the position indicating the measurement result on the matrix based on the determined rank of the subcutaneous fat mass and the rank of the visceral fat mass.

The writing part 59 performs a process of displaying the measurement result using the read format.

Figure 19:
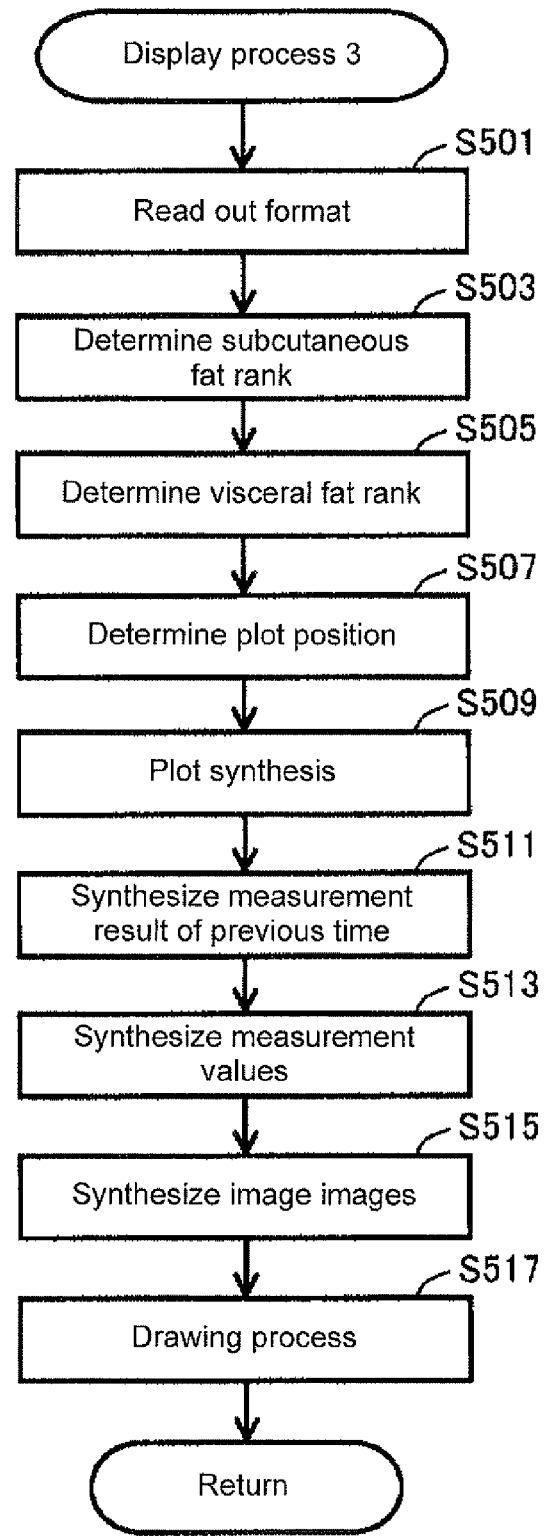
FIG. 19 is a flowchart showing a specific example (display process 3) of the display process of step S9 of FIG. 3 according to the third embodiment.

A specific example (display process 3) of the display process of step S9 according to the third embodiment will be described using FIG. 19. With reference to FIG. 19, the format reading part 57 reads out the format data of FIG. 18 in step S501.

In step S503, the subcutaneous fat rank determining part 51 compares the subcutaneous fat mass calculated in step S7 and the subcutaneous fat threshold value stored in the subcutaneous fat threshold storage part 294 to determine the rank to which the calculated subcutaneous fat belongs. Similarly, in step S505, the visceral fat rank determining part 53 compares the visceral fat mass calculated in step S7 and the visceral fat threshold value stored in the visceral fat threshold storage part 295 to determine the rank to which the calculated visceral fat belongs.

In step S507, the plot position determining part 55 determines the position defined with the rank determined in steps S503, S505 on the matrix configured by each index as the plot position, and in step S509, the writing part 59 performs image synthesis of the region 701 on the format of FIG. 18 read in step S501. Specifically, the writing part 59 performs image synthesis to display a CT image of a representative abdominal cross-section corresponded with each position in advance at each position of the matrix, and also display an image (circle image of solid line in the example of FIG. 20) indicating the plot position overlapping the CT image at a position corresponding to the plot position.

Figure 20:
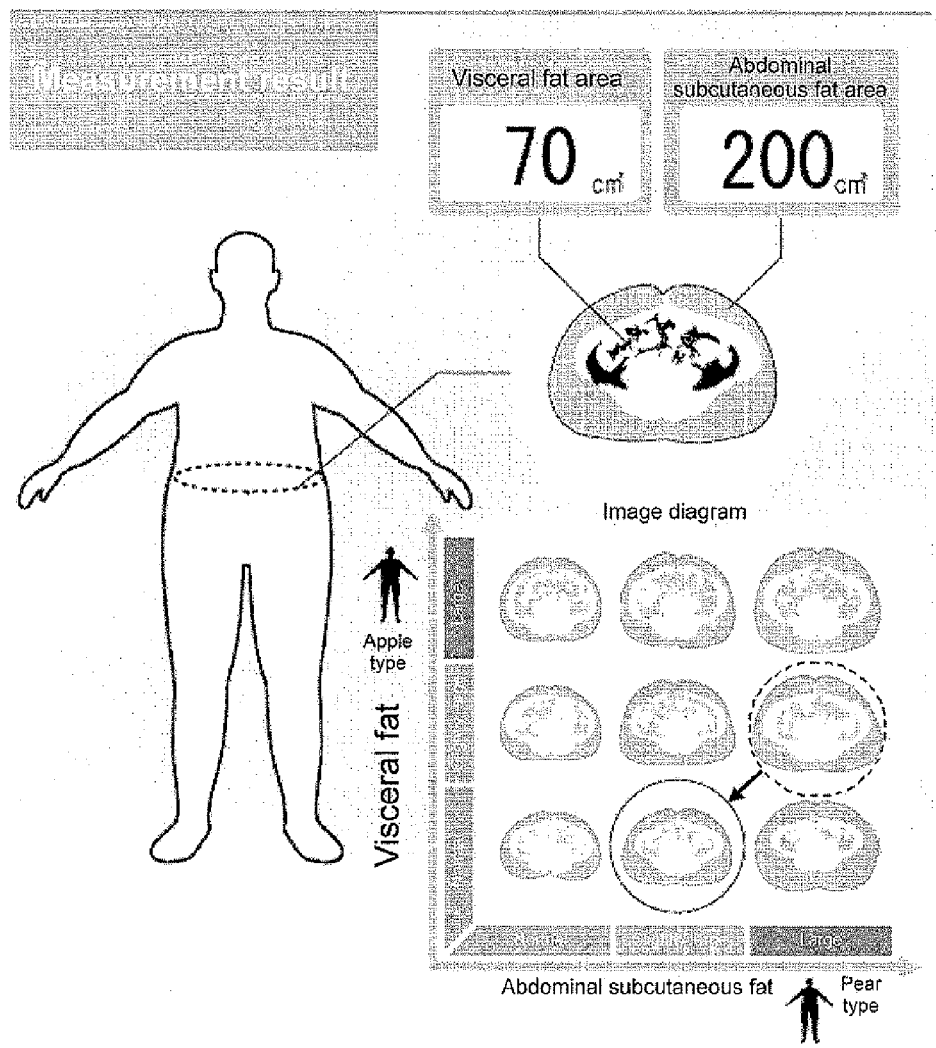
FIG. 20 is a view showing a specific example of a screen displayed by the display process 3.

In step S511, the subcutaneous fat mass and the visceral fat mass are read out as measurement results of the previous time stored in the measurement result storage part 296, the rank is determined thereon similar to steps S503 to S509, the plot position is determined, and the image synthesis is performed to display the image showing the plot position indicating the previous measurement result in an overlapping manner on the CT image at the corresponding position on the matrix, similar to step S509. The measurement result of the previous time is preferably shown with an image (circle image of dotted line in the example of FIG. 20) different from the measurement result of this time. As shown in FIG. 20, the image synthesis is more preferably carried out to display an image (arrow image in the example of FIG. 20) in which transition can be recognized in an overlapping manner from the position of the previous measurement result to the position of the measurement result of this time on the matrix. In step S511, the level determined based on the calculation result of this time and the level of the measurement result of the previous time are compared in the display processing portion 12, and the measurement result of the previous time may not be displayed if there is no difference between them, that is, if there is no change in the state of the abdominal fat from the previous time to this time.

In step S513, the writing part 59 synthesizes the format data to display each of the visceral fat mass and the subcutaneous fat mass calculated in step S7 in the regions 703, 704 of the format. Furthermore, in step S515, the writing part 59 reads out the corresponding image data and synthesizes the same to the format data to also display the CT image corresponded to the position corresponding to the position determined as the plot position in step S507 on the matrix in the region 702 of the format.

In step S517, the display processing portion 12 performs a process of drawing to define the format data for measurement result display obtained in the above processes as the display data, and terminates a series of processes.

When the display process 3 described above is executed in the display processing portion 12 of the device main body 100 according to the third embodiment, the measurement result of the subject can be displayed with a general tendency by only performing the process of comparing with the threshold value in the device main body 100. In this case, the tendency of the change in the subcutaneous fat, the visceral fat, and the like of the subject can be displayed by displaying the transition from the measurement result of the previous time as in the above example. Furthermore, as shown in FIG. 18, the CT image corresponding to the measurement result of the subject, that is, the CT image close to the abdominal cross-section of the subject can be provided even if the CT photographing function is not mounted on the device main body 100 or even if the CT photographing device is not connected by using the format displaying the representative CT image in advance. With such display, the measurer can visually grasp the state of the subcutaneous fat, the visceral fat, and the like of the subject compared to when displaying the measurement result with only numbers and graphs. Furthermore, the state of the subcutaneous fat, the visceral fat, and the like of the subject can be relatively grasped by comparing these states with other CT images. As a result, the motivation to improve the obesity or the center of the lifestyle related disease becomes effective on the subject.

In the case of the above example, the CT image of the abdominal cross-section is stored, but is not necessarily limited to the CT image itself of the subject, and may be an image synthesized as shown in the second embodiment.

As shown in FIG. 18, the measurer can more easily presume the state of the abdominal cross-section of the subject and the motivation to improve the obesity that is the center of the lifestyle related disease becomes effective on the subject by also displaying a human silhouette representing the approximate measurement position.

In the above example, the representative CT image of each position on the matrix is displayed in the region 701, but at least the CT image corresponded to the position corresponding to the position determined as the plot position in step S507 merely needs to be displayed, and only the CT image corresponded to the position corresponding to the position determined as the plot position and the CT image of the periphery thereof may be displayed.

The format of FIG. 18 is one example, and is not limited thereto. For instance, the measurement result of the subject is displayed at the position on the matrix in which the vertical axis is the rank of the visceral fat mass and the horizontal axis is the rank of the subcutaneous fat mass in the region 701, but the vertical and horizontal axes of the matrix are not limited to such contents, and may be the vertical and horizontal widths of the abdomen, the fat free mass, the ratio of the visceral fat mass and the subcutaneous fat mass, the peripheral length of the abdomen (waist peripheral length), or the like. In this case, the threshold value necessary for ranking the measurement value, or the like of the subject according to the vertical and horizontal axes of the matrix is assumed to be stored in the memory section 29. Furthermore, similar to the CT image corresponding to the measurement result of the subject displayed in the region 702, the image corresponding to the measurement result or the subject information such as sex and age may be set from the representative images stored in advance for the human silhouette shown in the region 705. The format merely needs to matrix display the measurement result including at least the region 701 of each region shown in FIG. 18, and may not include other regions.

The embodiments disclosed herein are illustrative in all aspects and should not be recognized as being restrictive. The scope of the invention is defined by the claims rather than by the description made above, and all modifications equivalent in meaning with the claims and within the scope of the claims are intended to be encompassed herein.

DESCRIPTION OF SYMBOLS 10 control section
11 calculation processing portion
12 display processing portion
21 constant current generating section
22 terminal switching section
23 potential difference detecting section
25 subject information inputting section
26 communication section
28 power supply section
29 memory section
31 outer shape ellipse determining part
33 correcting part
35 fat ellipse determining part
41 subcutaneous fat image selecting part
43 visceral fat image selecting part
45 determining part
47 synthesizing part
51 subcutaneous fat rank determining part
53 visceral fat rank determining part
55 plot position determining part
57 format reading part
59 writing part
100 device main body
110 display unit
111 impedance calculating part
112 fat mass calculating part
120 operation section
201, 202, 203, 204 clip
291 additional image DB
292 subcutaneous fat image DB
293 visceral fat image DB
294 subcutaneous fat threshold storage part
295 visceral fat threshold storage part
296 measurement result storage part
297 format storing part
300 belt
310 pushing member
320 belt portion
330 buckle
400 measurement unit
401 cursor supporting portion
401a horizontal width measurement cursor part
401b vertical width measurement cursor part
402 body build measuring portion
500 outlet
600 external device
701 to 705 region
AP1, AP2, AP3, AP4 abdominal electrode pair
H11, H21, F11, F21 electrode

The invention claimed is:

1. A health managing device comprising:
 a first measuring device which measures a vertical width and a horizontal width of an abdomen of a subject;
 a second measuring device which measures a fat value that is a value related to visceral fat, subcutaneous fat, and fat free mass of a subject using an impedance; and
 a display processing device which is configured to execute
  a process of displaying an abdominal cross-sectional image showing a shape corresponding to an outer shape of the abdomen of the subject and a shape corresponding to a state of fat of the abdomen on a display device as a process of specifying an abdominal cross-sectional image of the subject corresponding to measurement results of the first measuring device and the second measuring device, and display the same on the display device;
 wherein the display processing device includes:
  a first determining device, which is configured to determine an elliptical shape defined by a vertical width and a horizontal width measured by the first measuring device, and
  a second determining device, which is configured to determine an elliptical shape representing each of a visceral fat mass, a subcutaneous fat mass, and a fat free mass with respect to the elliptical shape based on a respective ratio of the visceral fat mass, the subcutaneous fat mass, and the fat free mass with respect to an abdominal cross-section of the subject.

2. The health managing device according to claim 1, wherein
 the display processing device further includes,
 a correction device, which is configured to correct an area corresponding to a position where the fat value is measured of the elliptical shape.

3. The health managing device according to claim 2, further comprising:
 a first non-transitory storage device, which stores figure data representing a subcutaneous fat in association with a proportion of the subcutaneous fat and the visceral fat;
 wherein the correction device is configured to correct the elliptical shape by extracting the figure data associated with the measured proportion of the subcutaneous fat and the visceral fat from the first storage device, and add a figure representing the subcutaneous fat indicated by the figure data to an area corresponding to the measured position of the elliptical shape.

4. The health managing device according to claim 2, further comprising:
 a first non-transitory storage device, which stores figure data representing a subcutaneous fat in association with the vertical width and the horizontal width of the abdomen;
 wherein the correction device is configured to correct the elliptical shape by extracting from the first storage device the figure data associated with the measured vertical width and the horizontal width of the abdomen of the subject, an area of the figure data corresponding to a difference between a sum of areas respectively indicating the measured visceral fat, the subcutaneous fat, and the fat free mass and the area of the elliptical shape, and add a figure representing the subcutaneous fat indicated by the figure data to an area corresponding to the measured position of the elliptical shape.

5. The health managing device according to claim 2, wherein the correction device is configured to correct the elliptical shape by moving in a normal direction by a length corresponding to information for every area corresponding to the position where the fat value is measured of the elliptical shape determined in the first determining device.

6. The health managing device according to claim 1, further comprising:
 a first electrode pair;
 a second electrode pair;

a current generating section which generates current to be supplied between electrodes of the first electrode pair; and a potential difference detecting section which detects a potential difference between electrodes of the second electrode pair with current flowing between the electrodes of the first electrode pair;

wherein the second measuring device calculates a visceral fat mass, a subcutaneous fat mass, and a fat free mass of the subject based on the potential difference detected by the first electrode pair for a body axis direction of the abdomen of the subject by flowing current to the second electrode pair.

7. A health managing device comprising:

a first measuring device which measures a vertical width and a horizontal width of an abdomen of a subject;

a second measuring device which measures a fat value, the fat value being related to visceral fat, subcutaneous fat, and fat free mass of a subject using an impedance;

a first non-transitory storage device, which stores a plurality of photographed images of the subcutaneous fat in association with the vertical width and the horizontal width of the abdomen of the subject and the measured fat value related to a subcutaneous fat mass of the subject;

a second non-transitory storage device, which stores a plurality of photographed images of the visceral fat in association with the vertical width and the horizontal width of the abdomen of the subject and the measured fat value related to a visceral fat mass of the subject; and a display processing device which is configured to execute a process of displaying an abdominal cross-sectional image showing a shape corresponding to an outer shape of the abdomen of the subject and a shape corresponding to a state of fat of the abdomen on a display device as a process of specifying an abdominal cross-sectional image of the subject corresponding to measurement results of the first measuring device and the second measuring device, and displaying on the display device;

wherein the display processing device includes:

a first extracting process of device, which is configured to extract one photographed image of the subcutaneous fat from the first storage device based on the measured vertical width and the horizontal width of the abdomen of the subject and at least measured information related to the subcutaneous fat of the subject;

a second extracting device, which is configured to extract one photographed image of the visceral fat from the second storage device based on the measured vertical width and the horizontal width of the abdomen of the subject and at least measured information related to the visceral fat of the subject; and the display device, which is configured to display an abdominal cross-sectional image based on the photographed image extracted in the first extracting device and the photographed image extracted in the second extracting device.

8. The health managing device according to claim 7, wherein the display device, is configured to synthesize by overlapping the photographed image of the visceral fat on the extracted photographed image of the subcutaneous fat.

9. The health managing device according to claim 7, wherein the fat value stored in association with the photographed image in the first storage device and the second storage device is at least one value selected from the measured visceral fat mass, the subcutaneous fat mass, the fat free mass of the subject, and a proportion by any combination of the measured visceral fat mass, the subcutaneous fat mass, and the fat free mass of the subject.

10. The health managing device according to claim 7, further comprising:

a first electrode pair;

a second electrode pair;

a current generating section which generates current to be supplied between electrodes of the first electrode pair; and a potential difference detecting section which detects a potential difference between electrodes of the second electrode pair with current flowing between the electrodes of the first electrode pair;

wherein the second measuring device calculates a visceral fat mass, a subcutaneous fat mass, and a fat free mass of the subject based on the potential difference detected by the first electrode pair for a body axis direction of the abdomen of the subject by flowing current to the second electrode pair.

11. A health managing device, comprising:

a first measuring device which measures a vertical width and a horizontal width of an abdomen of a subject;

a second measuring device which measures a fat value or a value related to visceral fat, subcutaneous fat, and fat free mass of a subject using an impedance;

a first non-transitory storage device which stores an image of the abdominal cross-section of each state defined with a first index and a second index respectively using one of a measurement result of the first measuring device or a measurement result of the second measuring device; and a display processing device which is configured to execute a process of specifying an abdominal cross-sectional image of the subject and displaying on a display device;

wherein the display processing device includes:

a rank determining device, which is configured to determine each rank of measured information on the first index and information on the second index, and an arranging device, which is configured to arrange the image corresponding to the measured information of the image stored in the first storage device and the image corresponding to at least a periphery in a space defining the first index and the second index as the vertical axis and the horizontal axis, and display the image corresponding to the measured information differently from other images.

12. The health managing device according to claim 11, wherein the arranging device is further configured to display a human silhouette correspondingly to the measured information.

13. The health managing device according to claim 11, wherein the arranging device is further configured to display a value representing the measurement result correspondingly to the measured information.

14. The health managing device according to claim 11, further comprising:

a second non-transitory storage device which stores the measurement result; wherein the arranging device is further configured to display an image corresponding to a measurement result of a previous time stored in the second storage device, an image corresponding to a measurement result of this time of the images stored in the first storage device differently from other images, and an image clearly indicating a transition in between.

15. The health managing device according to claim 11, wherein the first index and the second index are at least one of the following: the vertical width and the horizontal width of the abdominal cross-section, the information related to the visceral fat, the information related to the subcutaneous fat, the information related to the fat free mass, a ratio of the visceral fat mass and the subcutaneous fat mass, and an abdominal peripheral length.

16. The health managing device according to claim 11, further comprising:
  a first electrode pair;
  a second electrode pair;
  a current generating section which generates current to be supplied between electrodes of the first electrode pair; and
  a potential difference detecting section which detects a potential difference between electrodes of the second electrode pair with current flowing between the electrodes of the first electrode pair;
  wherein the second measuring device calculates a visceral fat mass, a subcutaneous fat mass, and a fat free mass of the subject based on the potential difference detected by the first electrode pair for a body axis direction of the abdomen of the subject by flowing current to the second electrode pair.

\* \* \* \* \*